US011939552B2

(12) United States Patent
Kreel et al.

(10) Patent No.: US 11,939,552 B2
(45) Date of Patent: *Mar. 26, 2024

(54) PROCESS OF RECOVERING OIL

(71) Applicant: Novozymes A/S, Bagsvaerd (DK)

(72) Inventors: Nathaniel Edward Kreel, Louisburg, NC (US); Joseph Mark Jump, Raleigh, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,465

(22) Filed: Sep. 22, 2022

(65) Prior Publication Data

US 2023/0044835 A1 Feb. 9, 2023

Related U.S. Application Data

(63) Continuation of application No. 17/147,623, filed on Jan. 13, 2021, now Pat. No. 11,505,765, which is a continuation of application No. 16/449,703, filed on Jun. 24, 2019, now Pat. No. 10,920,172, which is a continuation of application No. 15/956,274, filed on Apr. 18, 2018, now Pat. No. 10,731,104, which is a continuation of application No. 14/901,504, filed as application No. PCT/US2014/433392 on Jun. 20, 2014, now Pat. No. 10,035,973.

(60) Provisional application No. 61/991,866, filed on May 12, 2014, provisional application No. 61/943,794, filed on Feb. 24, 2014, provisional application No. 61/883,727, filed on Sep. 27, 2013, provisional application No. 61/838,650, filed on Jun. 24, 2013.

(51) Int. Cl.
| | |
|---|---|
| *C11B 13/00* | (2006.01) |
| *B01D 3/00* | (2006.01) |
| *C11B 3/00* | (2006.01) |
| *C12N 9/28* | (2006.01) |
| *C12N 9/34* | (2006.01) |
| *C12N 9/50* | (2006.01) |
| *C12N 9/52* | (2006.01) |
| *C12N 9/58* | (2006.01) |
| *C12P 7/10* | (2006.01) |
| *C12P 7/64* | (2022.01) |

(52) U.S. Cl.
CPC .............. *C11B 13/00* (2013.01); *C11B 3/003* (2013.01); *C12N 9/2417* (2013.01); *C12N 9/2428* (2013.01); *C12N 9/50* (2013.01); *C12N 9/52* (2013.01); *C12N 9/58* (2013.01); *C12P 7/10* (2013.01); *C12P 7/64* (2013.01); *B01D 3/002* (2013.01); *C12Y 302/01001* (2013.01); *C12Y 302/01003* (2013.01); *C12Y 304/00* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 5,192,677 A | 3/1993 | Kinsella et al. | |
| 5,705,379 A | 1/1998 | Wilson et al. | |
| 5,756,339 A | 5/1998 | Mitta | |
| 6,358,726 B1 | 3/2002 | Takakura | |
| 7,601,858 B2 | 10/2009 | Cantrell et al. | |
| 7,608,729 B2 | 10/2009 | Winsness et al. | |
| 7,820,419 B2 | 10/2010 | Smith et al. | |
| 8,008,517 B2 | 8/2011 | Cantrell | |
| 8,048,657 B2 | 11/2011 | Breneman et al. | |
| 9,677,095 B2 | 6/2017 | Deinhammer | |
| 9,816,112 B2 | 11/2017 | Deinhammer | |
| 9,951,364 B2 | 4/2018 | Kang et al. | |
| 10,035,973 B2 * | 7/2018 | Kreel | C12N 9/58 |
| 10,093,882 B2 * | 10/2018 | Clark | C12N 9/52 |
| 10,731,104 B2 * | 8/2020 | Kreel | C12N 9/50 |
| 10,781,398 B2 * | 9/2020 | Kreel | C12N 9/52 |
| 10,844,318 B2 * | 11/2020 | Clark | C12N 9/50 |
| 10,920,172 B2 * | 2/2021 | Kreel | C11B 13/00 |
| 11,499,170 B2 | 11/2022 | Deinhammer et al. | |
| 11,505,765 B2 * | 11/2022 | Kreel | C12N 9/50 |
| 11,566,266 B2 | 1/2023 | Deinhammer et al. | |
| 2002/0086402 A1 | 7/2002 | Takakura | |
| 2004/0057944 A1 | 3/2004 | Galle et al. | |
| 2004/0219649 A1 | 11/2004 | Olsen | |
| 2005/0084934 A1 | 4/2005 | Takukura | |
| 2005/0100996 A1 | 5/2005 | Lantero, Jr. | |
| 2007/0178567 A1 | 8/2007 | Lewis | |
| 2007/0184150 A1 | 8/2007 | Bhargava | |
| 2008/0138871 A1 | 6/2008 | Smith | |
| 2009/0227004 A1 | 9/2009 | Dale | |

(Continued)

FOREIGN PATENT DOCUMENTS

| | | |
|---|---|---|
| CN | 102361975 A | 2/2012 |
| CN | 102869771 A | 1/2013 |

(Continued)

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Fed. Cir. Case: 21-2184 re Rule 36 Affirmance of IPR 2020-00464 Final Written Decision dated Oct. 5, 2022.
IPR 2020-00464 re Patent 7,820,419 B2—Final Written Decision dated Jul. 20, 2021.
IPR 2019-01010 re Patent 10,035,973 B2—Granting Request for Adverse Judgment After Institution of Trial.
Sen et al, 2007, Appl Biochem Biotechnol 143(3), 212-223.
Chica et al, 2005, Curr Op Biotechnol 16(4), 378-384.
Gray et al, 1986, Uniprot access No. P00799.
Lao et al, 1998, Uniprot access No. O86984.

(Continued)

*Primary Examiner* — Christian L Fronda
(74) *Attorney, Agent, or Firm* — David A. Fazzolare

(57) ABSTRACT

The present invention relates to processes of recovering oil after liquefaction and/or from thin stillage and/or syrup/evaporated centrate from a fermentation product production process by adding a thermostable protease to the whole stillage, thin stillage and/or syrup.

24 Claims, 5 Drawing Sheets
Specification includes a Sequence Listing.

(56) References Cited

U.S. PATENT DOCUMENTS

| | | |
|---|---|---|
| 2010/0058649 A1 | 3/2010 | Bootsma |
| 2012/0040436 A1 | 2/2012 | Harada et al. |
| 2012/0214197 A1 | 8/2012 | Landvik et al. |
| 2014/0024064 A1 | 1/2014 | Burlew et al. |

FOREIGN PATENT DOCUMENTS

| | | |
|---|---|---|
| DE | 10 2005 062 984 A1 | 7/2007 |
| WO | 92/002614 A1 | 2/1992 |
| WO | 92/20777 A1 | 11/1992 |
| WO | 97/29179 A1 | 8/1997 |
| WO | 1999019467 A1 | 4/1999 |
| WO | 02/074895 A1 | 9/2002 |
| WO | 2003048353 A1 | 6/2003 |
| WO | 04/080923 A1 | 9/2004 |
| WO | 2004/087889 A1 | 10/2004 |
| WO | 2005052146 A2 | 6/2005 |
| WO | 2005052161 A2 | 6/2005 |
| WO | 2005/113785 A2 | 12/2005 |
| WO | 2006/086792 A2 | 8/2006 |
| WO | 07/056321 A1 | 5/2007 |
| WO | 2007098396 A2 | 8/2007 |
| WO | 2009/052101 A1 | 4/2009 |
| WO | 2009/100138 A2 | 8/2009 |
| WO | 2010/08841 A2 | 1/2010 |
| WO | 2011/072191 A2 | 6/2011 |
| WO | 2011068803 A1 | 6/2011 |
| WO | 2011/082425 A2 | 7/2011 |
| WO | 2011080353 A1 | 7/2011 |
| WO | 2011/126897 A2 | 10/2011 |
| WO | 2011/127802 A1 | 10/2011 |
| WO | 2012/084225 A1 | 6/2012 |
| WO | 2012/088303 A2 | 6/2012 |
| WO | 2013006756 A2 | 1/2013 |
| WO | 2013/082486 A1 | 6/2013 |
| WO | 2018/118815 A1 | 6/2018 |
| WO | 2018/169780 A1 | 9/2018 |

OTHER PUBLICATIONS

Maeder et al, 2002, Unirpot access No. Q8U0C9.
Silva et al, 1998, Uniprot access No. O31193.
Singh et al, 2017, Curr Protein and Peptide Science 18, 1-11.
WO 2003-48353 Access No. ABR62336.
IPR 2020-00464 re Patent 7,820,419 B2—Institution Decision dated Jul. 28, 2020.
Case No. IPR2020-00464, U.S. Pat. No. 7,820,419 dated Jan. 27, 2020.
Declaration of Douglas S. Clark, Ph.D. for IPR 2020-00464 dated Jan. 25, 2020.
Goode et al., Optimization of Mashing Conditions when Mashing with Unmalted Sorghum and Commercial Enzymes, 61 J. Am. Soc. Brew. Chem. 69-78 (2003).
K.C. Thomas & W.M. Ingledew, Fuel Alcohol Production: Effects of Free Amino Nitrogen on Fermentation of Very-High-Gravity Wheat Mashes, 56 Appl. Environ. Microbiology 2046-2050 (1990).
B. T. Little, Alternative Cereals for Beer Production, 7 FERMENT 163-168 (1994).
The Alcohol Textbook, Foreword, Chapters 1, 2, 14, 15 (K.A. Jacques et al., eds., 4th ed. 2003).
Declaration of Dr. Vijay Singh dated Feb. 24, 2019.
Ben et al, 2010—Uniport Access No. Q9KWY6.
Cheng et al, 2011, Appl Biochem Biotechnol 163(6), 693-706.
Niehaus et al, 1999, Appl Microbiol Biotechnol 51, 711-729.
Perez-Carillo et al, 2012, Biochem Eng J 67, 1-9.
Devos et al., 2000, "Practical Limits of Function Prediction," PROTEINS: Structure, Function, and Genetics 41:98-107 (Exhibit A).
Anonymous, 2006-2007, Biochemicals, reagents and kits of life science research.
Brock, 1967, Science 158(3804), 1012-1019.
Bruins et al, 2001, Appl Biochem Biotechnol 90, 155-186.
Connaris et al, 1991, J Gen Microbiol 137, 1193-1199.
Katrolia et al, 2012, Bioresource Technology 110, 578-586.
Kristjansson et al, 1990, Biochem J 270, 51-55.
Lao et al, 1996, Appl Environ Microbiol 62(11), 4256-4259.
Li (Ed), 2010, Tianjin Science and Technology Translation Publishing Company, 26-28—Trans.
Majoni et al, 2011, JAOCS 88(4) 523-532.
Prakash et al, 2013, Biomed research international, Article ID 264020, 1-8.
Qi, 2011, Zhengzhou university press, 118-119—Trans.
Sun et al, 2013, Food Safety 34(2), 72-77.
Melle et al, 2001, Microbiol Mol Biol Revs 65(1), 1-43.
Wang et al, 2009, J Agric Food Chem 57, 2302-2307.
Wang, 2008, Lipid technology 20(9), 203-207.
Ward et al, 2002, Archaea 1, 63-74.
Yang (Ed), 2013, Industrial patent analysis report, Intellectual property press 16, 79—Trans.
Yao et al, 2014, Journal of bioprocess engineering and biorefinery 3, 323-331.
Zheng (Ed), 2003, Science and Technology Literature Press, 96—Trans.
Zheng (Ed), 2009, Zhongshan University Press, 315—Trans.
WO 2011-127802 A1—Accession No. AZN72409.
U.S. Appl. No. 10/035,973, PTAB decision granting IPR petition.
U.S. Appl. No. 14/362,002—OAs dated May 24, 2016, Jan. 17, 2017, Mar. 9, 2018, Sep. 19, 2018, Sep. 9, 2019.
Exhibit A: Devos et al., Practical Limits of Function Prediction, PROTEINS: Structure, Function, and Genetics 41:98-107 (2000).

* cited by examiner

PROCESS OF RECOVERING OIL

CROSS-REFERENCE TO RELATED APPLICATIONS

This application is a continuation of U.S. application Ser. No. 17/147,623 filed Jan. 13, 2021, now U.S. Pat. No. 11,505,765, which is a continuation of U.S. application Ser. No. 16/449,703 filed Jun. 24, 2019, now U.S. Pat. No. 10,920,172, which is a continuation of U.S. application Ser. No. 15/956,274 filed Apr. 18, 2018, now U.S. Pat. No. 10,731,104, which is a continuation of U.S. application Ser. No. 14/901,504 filed Dec. 28, 2015, now U.S. Pat. No. 10,035,973, which is a 35 U.S.C. 371 national application of PCT/US2014/043392 filed Jun. 20, 2014, which claims priority or the benefit under 35 U.S.C. 119 of U.S. provisional application Nos. 61/838,650, 61/863,727, 61/943,794 and 61/991,866 filed Jun. 24, 2013, Aug. 8, 2013, Feb. 24, 2014 and May 12, 2014, respectively, the contents of which are fully incorporated herein by reference.

REFERENCE TO A SEQUENCE LISTING

This application contains a Sequence Listing in computer readable form. The contents of the electronic sequence listing created on Jun. 20, 2014, named SQ_Listing.txt and 24 KB in size, is hereby incorporated by reference in its entirety.

FIELD OF THE INVENTION

The present invention relates to processes of extracting/recovering oil from liquefied material as well as thin stillage and/or syrup at the backend of a fermentation product production process based on starch-containing material.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35 and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles). An increasing number of ethanol plants extract oil from the thin stillage and/or syrup/evaporated centrate as a by-product for use in biodiesel production or other biorenewable products.

Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation product to form whole stillage; separating the whole stillage into thin stillage and wet cake; and recovering oil from the thin stillage. The fermentation medium may further comprise a protease.

It is an object of the present invention to provide improved processes for increasing the amount of recoverable oil from fermentation product production processes.

SUMMARY OF THE INVENTION

The object of the present invention is to provide improved processes of extracting or recovering oil at the backend of a fermentation product production process, such as especially an ethanol production process.

Therefore, in the first aspect the invention relates to processes of recovering oil, comprising (a) converting a starch-containing material into dextrins with an alpha-amylase; optionally recovering oil during and/or after step (a)
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease having a thermostability value of more than 20% determined as Relative Activity at 80° C./70° C. is present and/or added in step (a) or any one of steps (d)-(e').

In an embodiment the protease may have a themostability of above 90%, above 100% at 85° C. as determined using the Zein-BCA assay as disclosed in Example 2.

In a preferred embodiment the protease is present in and/or added in starch-containing material converting step (a). In an embodiment the temperature in step (a) is above the initial gelatinization temperature, such as between 80-90° C., such as around 85° C. Steps (b) and (c) may be carried out simultaneously or sequentially. In an embodiment steps (a), (b) and (c) are carried our simultaneously or sequentially. When steps (a), (b) and (c) are carried out simultaneously, the temperature is below the initial gelatinization temperature, such as between 25-40° C., preferably around 32° C. in case of producing fermentation products such as ethanol.

In a preferred embodiment the protease is present in or added to the whole stillage in step (d) and/or to the thin stillage after separating whole stillage into thin stillage and wet cake in step (e), and/or to the syrup in step (e'). In such embodiments step (a) may be carried out at temperatures at or above the initial gelatinization temperature, such as between 80-90° C., or below the initial gelatinization temperature, such as between 25-40° C. In a preferred embodiment oil is recovered from the thin stillage and/or syrup/evaporated centrate, e.g., by extraction, such as hexane extraction or by using another oil recovery technology well-known in the art.

The protease may be any protease having a thermostability value, as defined herein, of more than 20% determined as Relative Activity. Determination of "Relative Activity" and "Remaining Activity" is determined as described in Example 1. In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In an embodiment the protease may have a themostability of above 90%, above 100% at 85° C. as determined using the Zein-BCA assay as disclosed in Example 2.

In an embodiment the protease is a thermostable variant of the parent metallo protease derived *Thermoascus aurantiacus* shown in SEQ ID NO: 3 herein, classified as EC 3.4.24.39, or one having a sequence identity thereto of at least 60%, at least 70%, at least 80%, at least 90%, at least 95%, at least 96%, at least 97%, at least 98%, at least 99%. Examples of protease variants are disclosed in the section "Proteases" below and in the Examples below. In a preferred embodiment the protease variant is selected from the group comprising the following substitutions:

A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L
(using SEQ ID NO: 3 for numbering).

All of these protease variants have a higher thermostability value (as defined herein) than the wild-type parent protease shown in SEQ ID NO: 3 herein.

In an additional embodiment the protease is a filamentous fungus, e.g., a protease classified as EC 3.4.23.23, such as derived from a strain of *Rhizomucor*, such as *Rhizomucor miehei*, such as the protease shown in SEQ ID NO: 9 or one having a sequence identity thereto of at least 60%, at least 70%, at least 80%, at least 90%, at least 95%, at least 96%, at least 97%, at least 98%, at least 99%.

In another preferred embodiment the protease is a thermostable protease derived from the bacterium, e.g., classified as EC 3.4.21.62, such as *Pyrococcus furiosus*, such as the protease shown in SEQ ID NO: 4 or one having a sequence identity thereto of at least 60%, at least 70%, at least 80%, at least 90%, at least 95%, at least 96%, at least 97%, at least 98%, at least 99%.

In an additional embodiment the protease is a bacterial serine protease, such as derived from a strain of *Thermobifida*, such as *Thermobifida fusca*, such as the protease shown in SEQ ID NO: 10 or one having a sequence identity thereto of at least 60%, at least 70%, at least 80%, at least 90%, at least 95%, at least 96%, at least 97%, at least 98%, at least 99%.

According to the invention the oil may be extracted/recovered from the liquefied starch-containing material during and/or after step (a), before saccharification in step (b). Therefore, the invention also relates to processes of recovering oil, comprising (a) converting a starch-containing material into dextrins with an alpha-amylase;
recovering oil during and/or after step (a)
(b) saccharifying the dextrins using a carbohydrate source generating enzyme to form a sugar;
(c) fermenting the sugar in a fermentation medium into a fermentation product using a fermenting organism; wherein a protease having a thermostability value of more than 20% determined as Relative Activity at 80° C./70° C. is present and/or added in step (a).

In such embodiment oil may not be extracted/recovered at the back-end as defined herein. However, in an embodiment oil is extracted both during and/or after step (a) and from the thin stillage and/or optionally the syrup/evaporated centrate.

In another aspect the invention relates to the use of a protease having a thermostability value of more than 20%, more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. for oil recovery from thin stillage and/or syrup at the backend of a fermentation product production process based on starch-containing material.

DETAILED DESCRIPTION OF THE INVENTION

Figure 1:
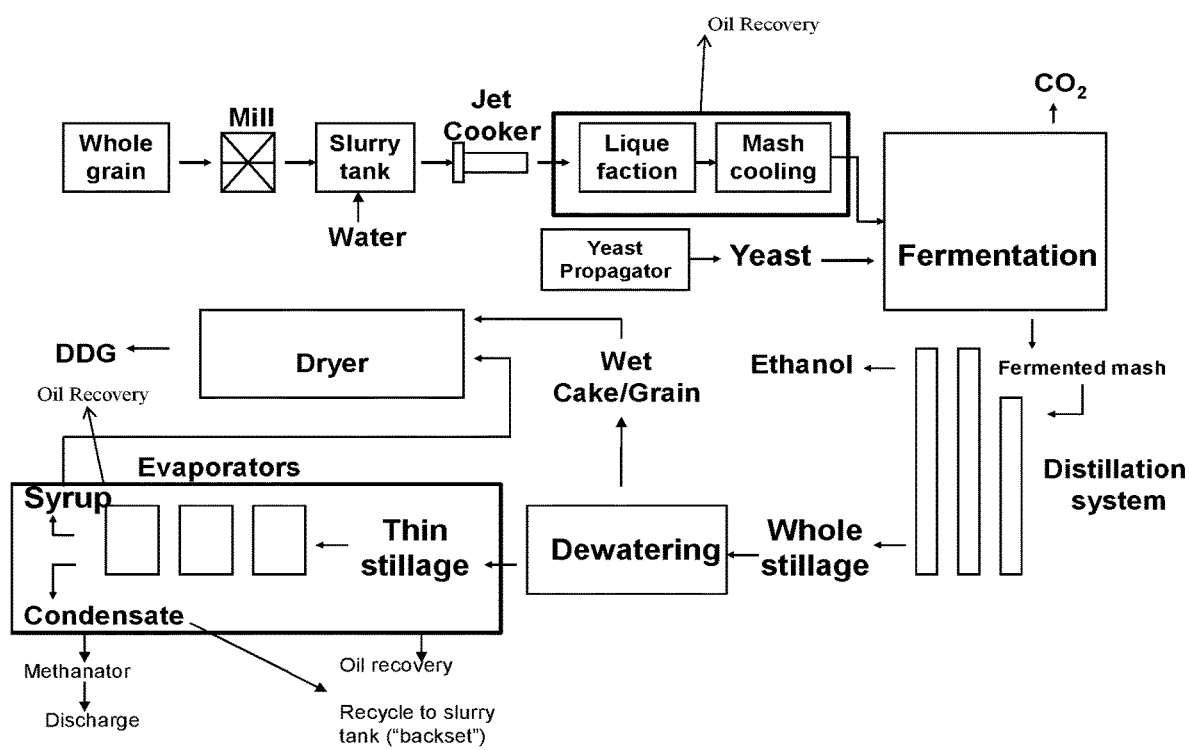
FIG. 1 schematically shows an ethanol production process. Oil may be recovered/extracted during and/or after liquefaction (step (a)), from the thin stillage and/or the syrup/centrate. The boxes in the figure indicate where oil may be recovered/extracted.

The object of the present invention is to provide improved processes of extracting or recovering oil at the backend of a fermentation product production process, such as especially an ethanol production process.

Therefore, in the first aspect the invention relates to processes of recovering oil, comprising (a) converting a starch-containing material into dextrins with an alpha-amylase; optionally recovering oil during and/or after step (a),
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease having a thermostability value of more than 20% determined as Relative Activity at 80° C./70° C. is present and/or added in step (a) or during any one of steps (d)-(e'). In an embodiment the protease may have a themostability of above 90%, above 100% at 85° C. as determined using the Zein-BCA assay as disclosed in Example 2.

In a preferred embodiment the protease is present in or added in starch-containing material converting step (a). In an embodiment the temperature is above the initial gelatinization temperature, such as between 80-90° C., such as around 85° C. In an embodiment step (a) is carried out as a liquefaction step followed by steps (b) and (c) carried out either simultaneously or sequentially. In a preferred embodiment steps (b) and (c) are carried out as a simultaneous saccharification and fermentation step (i.e., SSF).

In a preferred embodiment the oil recovering process of the invention comprises:
  (a) converting a starch-containing material into dextrins with an alpha-amylase at a temperature above the initial gelatinization temperature;
  (b) saccharifying the dextrins using a carbohydrate source generating enzyme to form a sugar;
  (c) fermenting the sugar in a fermentation medium into a fermentation product using a fermenting organism;
  (d) recovering the fermentation product to form a whole stillage;
  (e) separating the whole stillage into thin stillage and wet cake;
  (e') optionally concentrating the thin stillage into syrup;
  (f) recovering oil from the thin stillage and/or optionally the syrup, wherein a protease having a thermostability value of more than 20% determined as Relative Activity at 80° C./70° C. is present and/or added during step (a) or any of claims (d)-(e').

In another preferred embodiment the oil recovery process of the invention comprises:
  (a) converting a starch-containing material into dextrins with an alpha-amylase at a temperature below the initial gelatinization temperature;
  (b) saccharifying the dextrins using a carbohydrate source generating enzyme to form a sugar;
  (c) fermenting the sugar in a fermentation medium into a fermentation product using a fermenting organism;
  (d) recovering the fermentation product to form a whole stillage;
  (e) separating the whole stillage into thin stillage and wet cake;
  (e') optionally concentrating the thin stillage into syrup;
  (f) recovering oil from the thin stillage and/or optionally the syrup, wherein a protease having a thermostability value of more than 20% determined as Relative Activity at 80° C./70° C. is present and/or added during any of step (d)-(e').

In an embodiment steps (a), (b), and (c) are carried out simultaneously. This is typically done at a temperature below the initial gelatinization temperature, i.e. raw starch hydrolysis process (RSH). However, steps (a), (b), and (c) may also be carried out sequentially. In such embodiments step (a) may be carried out at temperatures at or above the initial gelatinization temperature, such as between 80-90° C., or below the initial gelatinization temperature, such as between 25-40° C., such as around 32° C.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C., Starch/Stärke, Vol. 44 (12) pp. 461-466 (1992).

In an embodiment the protease is present and/or added at the backend of a fermentation product production process, such as an ethanol production process, preferably to the whole stillage and/or syrup/evaporated centrate, including a conventional ethanol product production process, which included a liquefaction step, e.g., step (a) done at high temperatures, such as at temperatures at or above the initial gelatinization temperatures, such as at temperatures between 80-90° C., at a pH between 4.5 and 6.0, followed by simultaneous saccharification and fermentation (e.g., steps (b) and (c)) done a temperature between 25-40° C., such as around 32° C., if the fermentation product is ethanol or the like.

In another embodiment the protease is present and/or added at the backend of a fermentation product production process, such as an ethanol production process, preferably to the whole stillage and/or syrup, where granular starch is saccharified and fermented simultaneously at temperatures below the initial gelatinization temperatures, such as at temperatures between 25-40° C., at a pH between 4.5 and 6.0, i.e., steps (a) (b), and (c) are carried out simultaneously.

In a preferred embodiment the protease is present in or added to the whole stillage in step (d) and/or to the thin stillage after separating the whole stillage into thin stillage and wet cake in step (e), and/or to the syrup in step (e'). In a preferred embodiment oil is recovered from the thin stillage and/or syrup/evaporated centrate, e.g., by extraction, such as by hexane extraction or by using another oil recovery technology well-known in the art.

According to the invention the oil may be extracted from the liquefied starch-containing material during and/or after step (a), such as before saccharification in step (b). Therefore, the invention also relates to processes of recovering oil, comprising
  (b) converting a starch-containing material into dextrins with an alpha-amylase;
    recovering oil during and/or after step (a)
  (b) saccharifying the dextrins using a carbohydrate source generating enzyme to form a sugar;
  (c) fermenting the sugar in a fermentation medium into a fermentation product using a fermenting organism; wherein a protease having a thermostability value of more than 20% determined as Relative Activity at 80° C./70° C. is present and/or added in step (a).

In such embodiment oil may not be extracted at the back-end as defined herein. However, in an embodiment oil is extracted both during and/or after step (a) and from the thin stillage and/or optionally the syrup/evaporated centrate.

The protease may be any protease having a thermostability value, as defined herein, of more than 20% and the Example 1.

In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the metallo protease derived from *Thermoascus aurantiacus* shown in SEQ ID NO: 3 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the metallo protease derived from *Thermoascus aurantiacus* shown in SEQ ID NO: 3 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the metallo protease derived from *Thermoascus aurantiacus* shown in SEQ ID NO: 3 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In an embodiment the protease is a thermostable variant of the metallo protease derived *Thermoascus aurantiacus* shown in SEQ ID NO: 3 herein, or one having a sequence identity thereto of at least 60%, at least 70%, at least 80%, at least 90%, at least 95%, at least 96%, at least 97%, at least 98%, at least 99%. Examples of protease variants are disclosed in the section "Proteases" below and in the Examples below. In a preferred embodiment the protease variant is selected from the group of variants comprising the following substitutions:

A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L
(using SEQ ID NO: 3 for numbering).

All of these protease variants have higher thermostability value (as defined herein) than the wild-type parent protease shown in SEQ ID NO: 3 herein.

In an additional embodiment the protease is a filamentous fungus, e.g., derived from a strain of *Rhizomucor*, such as *Rhizomucor miehei*, such as the protease shown in SEQ ID NO: 9 or one having a sequence identity thereto of at least 60%, at least 70%, at least 80%, at least 90%, at least 95%, at least 96%, at least 97%, at least 98%, at least 99%.

In one embodiment the protease is derived from a strain of *Rhizomucor miehei*, such as the protease shown in SEQ ID NO: 9 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is derived from a strain of *Rhizomucor miehei*, such as the protease shown in SEQ ID NO: 9 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is derived from a strain of *Rhizomucor miehei*, such as the protease shown in SEQ ID NO: 9 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In another preferred embodiment the protease is a thermostable protease derived from the bacterium *Pyrococcus furiosus*, such as the protease shown in SEQ ID NO: 4, or one having sequence identity thereto of at least 60%, at least 70%, at least 80%, at least 90%, at least 95%, at least 96%, at least 97%, at least 98%, at least 99%.

The *Pyrococcus furiosus* protease shown in SEQ ID NO: 4 herein is a thermostable bacterial protease. A commercial *Pyrococcus furiosus* protease product (Pfu S) from Takara Bio Inc. (Japan) have been found to have a thermostability value of 110% (80° C./70° C.) and 103% (90° C./70° C.) at pH 4.5 determined as described in Example 1 herein.

In one embodiment the protease is a thermostable protease derived from the bacterium *Pyrococcus furiosus*, such as the protease shown in SEQ ID NO: 4 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is a thermostable protease derived from the bacterium *Pyrococcus furiosus*, such as the protease shown in SEQ ID NO: 4 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is a thermostable protease derived from the bacterium *Pyrococcus furiosus*, such as the protease shown in SEQ ID NO: 4 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In an additional embodiment the protease is a bacterial serine protease, such as derived from a strain of *Thermobifida*, such as *Thermobifida fusca*, such as the protease shown in SEQ ID NO: 10 or one having a sequence identity thereto of at least 60%, at least 70%, at least 80%, at least 90%, at least 95%, at least 96%, at least 97%, at least 98%, at least 99%.

In one embodiment the protease is derived from a strain of *Thermobifida*, such as *Thermobifida fusca*, such as the protease shown in SEQ ID NO: 10 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is derived from a strain of *Thermobifida*, such as *Thermobifida fusca*, such as the protease shown in SEQ ID NO: 10 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

In one embodiment the protease is derived from a strain of *Thermobifida*, such as *Thermobifida fusca*, such as the protease shown in SEQ ID NO: 10 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70.

When step (a) is carried out as a liquefaction step at high temperatures, i.e., above the initial gelatinization temperature, such as at temperatures between 80-90° C., such as around 85° C., the alpha-amylase may be a bacterial alpha-amylase. In an embodiment the pH in step (a) is from 4-7, preferably 4.5-6.

In an embodiment a jet-cooking step is carried out before in step (a). Jet-cooking may be carried out at a temperature between 95-140° C. for about 1-15 minutes, preferably for about 3-10 minutes, especially around about 5 minutes.

In a preferred embodiment a process of the invention further comprises, before step (a), the steps of:
  i) reducing the particle size of the starch-containing material, preferably by dry milling;
  ii) forming a slurry comprising the starch-containing material and water.

In a preferred embodiment the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular a *Bacillus stearothermophilus* alpha-amylase truncated to have from 485-495 amino acids, such as around 491 amino acids.

In a preferred embodiment the bacterial alpha-amylase is selected from the group of *Bacillus stearothermophilus* alpha-amylase variants comprising a double deletion, such as I181*+G182*, or I181*+G182*+N193F (using SEQ ID NO: 1 for numbering).

In a preferred embodiment the bacterial alpha-amylase is selected from the group of *Bacillus stearothermophilus* alpha-amylase variants:
  I181*+G182*+N193F+E129V+K177L+R179E;
  181*+G182*+N193F+V59A+Q89R+E129V+K177L+ R179E+H208Y+K220P+N224L+Q254S;
  I181*+G182*+N193F+V59A  Q89R+E129V+K177L+ R179E+Q254S+M284V; and
  I181*+G182*+N193F+E129V+K177L+R179E+K220P+ N224L+S242Q+Q254S (using SEQ ID NO: 1 for numbering).

The parent *Bacillus stearothermophilus* alpha-amylase may be the one shown in SEQ ID NO: 1 or may be one having sequence identity thereto of at least 60%, at least 70%, at least 80%, at least 90%, at least 95%, at least 96%, at least 97%, at least 98%, at least 99%.

A *Bacillus stearothermophilus* alpha-amylase variant may be a variant of the one shown in SEQ ID NO: 1 or may be one having sequence identity thereto of at least 60%, at least 70%, at least 80%, at least 90%, at least 95%, at least 96%, at least 97%, at least 98%, at least 99%, but less than 100%. In an embodiment the *Bacillus stearothermophilus* alpha-amylase variant has from 1-12 mutations, such as 1, 2, 3, 4, 5, 6, 7, 8, 9, 10, 11, 12 mutations, compared to the parent alpha-amylase, especially the parent alpha-amylase shown in SEQ ID NO: 1.

Step (a) is followed by saccharification of dextrins in step (b). However, a process of the invention may further comprise a pre-saccharification step, i.e., after step (a), but before saccharification step (b), carried out for 40-90 minutes at a temperature between 30-65° C.

According to the invention saccharification is carried out at a temperature from 20-75° C., preferably from 40-70° C., such as around 60° C., and at a pH between 4 and 5.

In a preferred embodiment fermentation step (c) or simultaneous saccharification and fermentation (SSF) (i.e., combined steps (b) and (c)) are carried out carried out at a temperature from 25° C. to 40° C., such as from 28° C. to 35° C., such as from 30° C. to 34° C., preferably around about 32° C. In an embodiment fermentation step (c) or simultaneous saccharification and fermentation (SSF) (i.e., combined steps (b) and (c)) are ongoing for 6 to 120 hours, in particular 24 to 96 hours. In an embodiment the starch-containing material converting step (a), saccharification step (b) and fermentation step (c) are carried out simultaneously or sequentially. In an embodiment the starch-containing material converting step (a) is carried out at a temperature below the initial gelatinization temperature, preferably from 20-60° C., such as 25-40° C., such as around 30-34° C., such as around 32° C. In an embodiment the starch-containing material is converted to dextrins and the dextrins are saccharified to a sugar by treating the starch-containing material with an alpha-amylase and glucoamylase below the initial gelatinization temperature of the starch-containing material. In an embodiment the conversion of the starch-containing material to dextrins, the saccharification of the dextrins to sugars, and the fermentation of the sugars are carried out in a single step (i.e., raw starch hydrolysis step). When the process of the invention is carried out as a raw starch hydrolysis process (i.e., single step process or no-cook process) the glucoamylase may preferably be derived from a strain of *Trametes*, such as a strain of *Trametes cingulata*, or a strain of *Athelia*, such as a strain of *Athelia rolfsii*. Preferred alpha-amylases used in a raw starch hydrolysis process include alpha-amylases derived from a strain *Rhizomucor*, such as a strain of *Rhizomucor pusillus*, such as a *Rhizomucor pusillus* alpha-amylase with a starch-binding domain (SBD), such as a *Rhizo mucor* pusillus alpha-amylase with *Aspergillus niger* glucoamylase linker and SBD. Generally the starch-containing material in raw starch hydrolysis processes (i.e., no-cook processes) are granular starch. Said granular starch may be reduced the particle size, preferably by milling, to from 0.05 to 3.0 mm, preferably 0.1-0.5 mm. Also the sugar level, such as glucose level, may be kept below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. The pH may be from 4-7, preferably 4.5-6.0, when conversion of the starch-containing material to dextrins, the saccharification of the dextrins to a sugar, and the fermentation of the sugar are carried out in a single step.

If the process of the invention is carried out as a conventional process (i.e., step (a) is carried out as a liquefaction step at a temperature above the gelatinization temperature) the carbohydrate-source generating enzyme used in step (b) is preferably a glucoamylase derived from *Aspergillus*, preferably *A. niger, A. awamori*, or *A. oryzae*; or a strain of *Trichoderma*, preferably *Trichoderma reesei*; or a strain of *Talaromyces*, preferably *Talaromyces emersonii*, or a strain of *Pycnoporus*, or a strain of Gloephyllum.

Examples of other suitable glucoamylase can be found below in the "Glucoamylases" section below.

Generally the starch-containing material in step (a), including granular starch, contains 20-55 wt.-% dry solids, preferably 25-40 wt.-% dry solids, more preferably 30-35% dry solids.

In an embodiment of the invention the protease is present in or added to the whole stillage in step (d) and/or the thin stillage, in step (e) or after separation in step (e), and/or the syrup in step (e'). Separation (i.e. dewatering) in step (e) may be carried out by centrifugation, preferably a decanter centrifuge, filtration, preferably using a filter press, a screw press, a plate-and-frame press, a gravity thickener or decker or any other separation technology known in the art. In an embodiment the starch-containing material is cereal. In an embodiment the starch-containing material is selected from the group consisting of corn, wheat, barley, cassava, sorghum, rye, potato, beans, milo, peas, rice, sago, sweet potatoes, tapioca, or any combination thereof.

The (desired) fermentation product may in an embodiment be selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., H2 and CO2), and more complex compounds, including, for example, antibiotics (e.g., penicillin and tetracycline); enzymes; vitamins (e.g., riboflavin, B12, beta-carotene); and hormones. In a preferred embodiment the (desired) fermentation product is ethanol. According to the invention the desired fermentation product may be recovered by distillation. According to the invention oil may be recovered from the thin stillage and/or syrup/evaporated centrate, e.g., by extraction, such as hexane extraction.

In a specific embodiment the process of the invention relates to recovering oil comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') concentrating the thin stillage into syrup;
(f) recovering oil from the syrup, wherein a protease having a thermostability value of more than 20% determined as Relative Activity at 80° C./70° C. is present and/or added in step (e').

In another specific embodiment the process of recovering oil comprises (a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) optionally recovering the fermentation product to form a whole stillage;
(e) optimally separating the whole stillage into thin stillage and wet cake;
(e') optionally concentrating the thin stillage into syrup;
wherein a protease having a thermostability value of more than 20% determined as Relative Activity at 80° C./70° C. is present and/or added in step (a) and/or steps (d)-(e') and oil is recovered during and/or after step (a).

In another specific embodiment the process of recovering oil comprises
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product;
wherein a protease having a thermostability value of more than 20% determined as Relative Activity at 80° C./70° C. is present and/or added in step (a) and oil is recovered during and/or after step (a).

In another specific embodiment the process of recovering oil comprises
(a) converting a starch-containing material into dextrins with an alpha-amylase and *Pyrococcus furiosus* protease;
(b) saccharifying the dextrins using a carbohydrate source generating enzyme to form a sugar;
(c) fermenting the sugar in a fermentation medium into a fermentation product using a fermenting organism;
(d) recovering the fermentation product, wherein oil is recovered during and/or after step (a).

After step (a) means after step (a) and before saccharification in step (b).

In a preferred embodiment the protease is derived from a strain of *Pyrococcus*, preferably a strain of *Pyrococcus furiosus*, such as the one shown in SEQ ID NO: 1 in U.S. Pat. No. 6,258,726 or SEQ ID NO: 4 herein. In an embodiment the protease has at least 60%, such as at least 70%, such as at least 80%, such as at least 85%, such as at least 90%, such as at least 95%, such as at least 96%, such as at least 97%, such as at least 98%, such as at least 99% sequence identity to SEQ ID NO: 1 in U.S. Pat. No. 6,258,726 or SEQ ID NO: 4 herein. Other contemplated proteases are described in the "Proteases" section below.

Use of Thermostable Protease for Improving Oil Extraction

In an aspect, the invention relates to the use of a protease having a thermostability value of more than 20%, more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. for increasing oil recovery yields from thin stillage and/or syrup in a fermentation product production process. In an embodiment the protease may have a themostability of above 90%, above 100% at 85° C. as determined using the Zein-BCA assay as disclosed in Example 2.

Separating (Dewatering) Whole Stillage into Thin Stillage and Wet Cake in Step (e)

Separating whole stillage into thin stillage and wet cake in step (e), in order to remove a significant portion of the liquid/water, may be done using any suitable separation technique, including centrifugation, pressing and filtration. In a preferred embodiment the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment the separation is carried out using other conventional separation equipment such as a plate/frame filter presses, belt filter presses, screw presses, gravity thickeners and deckers, or similar equipment.

Drying of Wet Cake

After the wet cake, containing about 30-35 wt.-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS).

Fermenting Organisms

Examples of fermenting organisms used in step c) for fermenting sugars in a fermentation medium into a desired fermentation product include fungal organisms, such as especially yeast. Preferred yeast includes strains of *Saccharomyces* spp., in particular, *Saccharomyces cerevisiae*.

In one embodiment the fermenting organism is added to the fermentation medium, so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED☐ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., H2 and CO2); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel, that typically is blended with gasoline. However, in the case of ethanol it may also be used as potable ethanol.

Recovery

Subsequent to fermentation the fermentation product, such as ethanol may be separated from the fermentation medium, e.g., by distillation. Alternatively the desired fermentation product may be extracted from the fermentation medium by micro or membrane filtration techniques. The fermentation product may also be recovered by stripping or other method well known in the art.

Enzymes

One or more of the following enzyme activities may be used according to the invention.

Proteases

According to the invention a thermostable protease (as defined herein) may be present of added during step (a) or steps (d)-(e').

The protease may be of any origin as long as it has a thermostability value as defined herein of more than 20% and the Example 1. In an embodiment the protease is of fungal origin. In another embodiment the protease is of bacterial origin. In an embodiment protease has a thermostability of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In another embodiment the protease has a thermostability value between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability value between 10 and 50%, such as between 10 and 30%, such as between 10 and 25% determined as Relative Activity at 85° C./70° C.

In an embodiment the protease has a thermostability value between 50 and 110%, such as between 70 and 110%, such as between 90 and 110% determined as Relative Activity at 85° C./70° C. In an embodiment the protease may have a themostability of above 90%, above 100% at 85° C. as determined using the Zein-BCA assay as disclosed in Example 2.

Fungal Proteases

In an embodiment the protease is of fungal origin.

In a preferred embodiment the protease is a variant of the metallo protease derived from a strain of the genus *Ther-* moascus, preferably a strain of *Thermoascus aurantiacus*, especially *Thermoascus aurantiacus* CGMCC No. 0670.

In an embodiment the protease is a variant of the metallo protease disclosed as the mature part of SEQ ID NO: 2 disclosed in WO 2003/048353 or SEQ ID NO: 3 herein.

In an embodiment the parent protease has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as least 100% identity to the mature part of the polypeptide of SEQ ID NO: 2 disclosed in WO 2003/048353 or SEQ ID NO: 3 herein.

In an embodiment the protease variant has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or SEQ ID NO: 3 herein.

In an embodiment the protease is a variant shown in any of Tables 1-4 in Examples 1 or 2 having a thermostability value of more than 20%, more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

This includes the protease variants of the wild-type protease shown in SEQ ID NO: 3, having the following substitutions:

D79L+S87P+A112P+D142L
D79L+Y82F+S87P+A112P+D142L
S38T+D79L+S87P+A112P+A126V+D142L
D79L+Y82F+S87P+A112P+A126V+D142L
A27K+D79L+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
S70V+D79L+Y82F+S87G+Y97W+A112P+D142L
D79L+Y82F+S87G+Y97W+D104P+A112P+D142L
S70V+D79L+Y82F+S87G+A112P+D142L
D79L+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L
A27K Y82F S87G D104P A112P A126V D142L
A27K D79L Y82F D104P A112P A126V D142L
A27KY82F D104PA112PA126V D142L

In a preferred embodiment the protease is a variant of the *Thermoascus aurantiacus* protease shown in SEQ ID NO: 3 herein with mutations selected from the group consisting of:
A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L.

In an additional embodiment the protease is a filamentous fungus, e.g., derived from a strain of *Rhizomucor*, such as *Rhizomucor miehei*, such as the protease shown in SEQ ID NO: 9 or one having a sequence identity thereto of at least 60%, at least 70%, at least 80%, at least 90%, at least 95%, at least 96%, at least 97%, at least 98%, at least 99%.

Bacterial Proteases

In an embodiment the protease is of bacterial origin.

In a preferred embodiment the protease is derived from a strain of *Pyrococcus*, preferably a strain of *Pyrococcus furiosus*.

In a preferred embodiment the protease is the one shown in SEQ ID NO: 1 in U.S. Pat. No. 6,258,726 or SEQ ID NO: 4 herein.

In an embodiment the protease has at least 60%, such as at least 70%, such as at least 80%, such as at least 85%, such as at least 90%, such as at least 95%, such as at least 96%, such as at least 97%, such as at least 98%, such as at least 99% sequence identity to SEQ ID NO: 1 in U.S. Pat. No. 6,258,726 or SEQ ID NO: 4 herein.

In an embodiment the protease is present and/or added in an effective amount in step (a) or any of steps (d)-(e'). In an embodiment of the invention the protease is added in a concentration of 0.01-100, such 0.1-10 micro g/g DS.

Alpha-Amylases

The method of the invention, including step (a), may be carried out using any suitable alpha-amylase. In a preferably embodiment a bacterial alpha-amylase and/or a fungal alpha-amylase may be used.

In an embodiment the alpha-amylase is bacterial when step (a) is carried out as a liquefaction step at high temperatures, i.e., above the initial gelatinization temperature.

In an embodiment the alpha-amylase is fungal when step (a) is carried out at a temperature below the initial gelatinization temperature, such as when steps (a), (b) and (c) are carried out as a raw starch hydrolysis (single step process or no-cook process) as described above.

Bacterial Alpha-Amylases

Examples of suitable bacterial alpha-amylases include the below mentioned. Preferred bacterial alpha-amylases used in step i) may be derived from a strain the genus *Bacillus* (sometimes referred to as *Geobacillus*), including a strain of *Bacillus licheniformis, Bacillus amyloliquefaciens, Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO:3 disclosed in WO 99/19467.

In an embodiment the *Bacillus stearothermophilus* alpha-amylase is one disclosed in WO 2011/082425, such as one selected from the group of:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

In an embodiment the *Bacillus stearothermophilus* alpha-amylase has the following mutations: 181*+G182*+N193F+V59A+Q89R+E129V+K177L+R179E+Q254S+M284V (SEQ ID NO: 1).

The truncated *Bacillus stearothermophilus* alpha-amylase are typically naturally truncated to be about 491 amino acids long, such as from 485-495 amine acids long.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T491+G107A+H156Y+A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TERMAMYL™ SC, LIQUOZYME™ SC, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, USA), FUELZYME™ (Verenium, USA).

A bacterial alpha-amylase may be added in step (a) in amounts as are well-known in the art. When measured in KNU units (described below in the "Materials & Methods"- section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in co-pending U.S. patent application No. 60/638,614, including Fungamyl variant with catalytic domain JA118 and *Athelia rolfsii* SBD (SEQ ID NO: 2 herein and SEQ ID NO:100 in U.S. 60/638,614), *Rhizomucor pusillus* alpha-amylase with *Athelia rolfsii* AMG linker and SBD (SEQ ID NO: 3 herein and SEQ ID NO:101 in U.S. 60/638,614), *Rhizo mucor pusillus* alpha-amylase with *Aspergillus niger* glucoamylase linker and SBD (which is disclosed in Table 5 as a combination of amino acid sequences SEQ ID NO:20 SEQ ID NO:72 and SEQ ID NO:96 in U.S. application Ser. No. 11/316,535 and further as SEQ ID NO: 13 herein), and *Meripilus giganteus* alpha-amylase with *Athelia rolfsii* glucoamylase linker and SBD (SEQ ID NO: 4 herein and SEQ ID NO:102 in U.S. 60/638,614). Other specifically contemplated hybrid alpha-amylases are any of the ones listed in Tables 3, 4, 5, and 6 in Example 4 in US application Ser. No. 11/316,535 or (WO 2006/069290) (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain. An acid alpha-amylases may according to the invention be added in an amount of 0.1 to 10 AFAU/g DS, preferably 0.10 to 5 AFAU/g DS, especially 0.3 to 2 AFAU/g DS.

Fungal alpha-amylases may be added to step (a) in a well know effective amount, preferably in the range from 0.001-1 mg enzyme protein per g DS (in whole stillage), preferably 0.01-0.5 mg enzyme protein per g DS.

Carbohydrate-Source Generating Enzyme

According to the invention a carbohydrate-source generating enzyme, preferably a glucoamylase, may be present and/or added during saccharification step (b) or simultaneous saccharification and fermentation.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is a glucoamylase.

Glucoamylases

The process of the invention, including step (b), may be carried out using any suitable glucoamylase. In a preferably embodiment the glucoamylase is of bacterial or fungal origin.

Contemplated glucoamylases include those from the group consisting of *Aspergillus* glucoamylases, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Ser. No. 10/992,187 (hereby incorporated by reference) or sequences having at least 80% or at least 90% identity thereto.

In a preferred embodiment the glucoamylase is derived from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*.

In an embodiment the glucoamylase present and/or added during saccharification and/or fermentation is of fungal origin, preferably from a strain of *Pycnoporus*, or a strain of *Gloephyllum*.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 18 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 15 herein.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS.

Glucoamylase may be added in an effective amount, preferably in the range from 0.001-1 mg enzyme protein per g DS, preferably 0.01-0.5 mg enzyme protein per g dry substrate.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Enzymes:

Alpha-Amylase LSCDS ("LSCDS"): *Bacillus stearothermophilus* alpha-amylase with the mutations: I181*+G182*+N193F truncated to 491 amino acids (SEQ ID NO: 1 herein).

Alpha-Amylase 369: (AA369): *Bacillus stearothermophilus* alpha-amylase with the mutations: I181*+G182*+N193F+V59A+Q89R+E129V+K177L+R179E+Q254S+M284V truncated to 491 amino acids (SEQ ID NO: 1 herein).

Protease TA ("TA"): Metallo protease derived from *Thermoascus aurantiacus* CGMCC No. 0670 disclosed as amino acids 1-177 in SEQ ID NO: 3 herein Protease 196 ("TA 196"): Metallo protease derived from *Thermoascus aurantiacus* CGMCC No. 0670 disclosed as amino acids 1-177 in SEQ ID NO: 3 herein with the following mutations: A27K+D79L+Y82F+S87G+D104P+A112P+A126V+D142L.

Protease PF ("PF"): Protease derived from the bacterium *Pyrococcus furiosus* shown in SEQ ID NO: 4 herein.

Protease RH ("RH"): Protease derived from a filamentous fungus *Rhizomucor miehei* shown in SEQ ID NO: 9 herein.

Protease TF ("TF"): Protease derived from a filamentous fungus *Thermobifida fusca* shown in SEQ ID NO: 10 herein.

Glucoamylase SF is a glucoamylase derived from a strain of *Talaromyces emersonii* and is disclosed in WO9928448 and is available from Novozymes A/S.

Glucoamylase TC is a glucoamylase derived from *Trametes cingulata* disclosed in SEQ ID NO: 2 of WO 2006/069289 and available from Novozymes A/S.

Alpha-amylase JA is an alpha-amylase derived from *Rhizomucor pusillus* and disclosed as V039 in Table 5 in WO 2006/069290.

Determination of Alpha-Amylase Activity

1. Phadebas™ Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units. In this absorbance range there is linearity between activity and absorbance (Lambert-Beer law). The dilution of the enzyme must therefore be adjusted to fit this criterion. Under a specified set of conditions (temperature, pH, reaction time, buffer conditions) 1 mg of a given alpha-amylase will hydrolyze a certain amount of substrate and a blue colour will be produced. The measured absorbance is directly proportional to the specific activity (activity/mg of pure alpha-amylase protein) of the alpha-amylase in question under the given set of conditions.

2. Alternative Method

Alpha-amylase activity is alternatively determined by a method employing the PNP-G7 substrate. PNP-G7 which is a abbreviation for p-nitrophenyl-alpha,D-maltoheptaoside is a blocked oligosaccharide which can be cleaved by an endo-amylase. Following the cleavage, the alpha-glucosidase included in the kit digest the substrate to liberate a free PNP molecule which has a yellow colour and thus can be measured by visible spectophometry at wavelength Lambda=405 nm (400-420 nm). Kits containing PNP-G7 substrate and alpha-glucosidase is manufactured by Bohringer-Mannheim (cat. No. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-glucosidase solution with 0.5 ml substrate.

The assay is performed by transforming 20 microL enzyme solution to a 96 well microtitre plate and incubating at 25° C. 200 microL working solution, 25° C. is added. The solution is mixed and pre-incubated 1 minute and absorption is measured every 15 seconds over 3 minutes at OD 405 nm.

The slope of the time dependent absorption-curve is directly proportional to the specific activity (activity per mg enzyme) of the alpha-amylase in question under the given set of conditions.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
|---|---|
| Temperature | 37° C. |
| pH | 4.7 |
| Reaction time | 7-20 minutes |

A detailed description of Novozymes' method for determining KNU and FAU is available on request as standard method EB-SM-0009.02/01.

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S). The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

| | Alpha-amylase | |
|---|---|---|
| Starch + Iodine | → | Dextrins + Oligosaccharides |
| | 40° C., pH 2.5 | |
| Blue/violet | | t = 23 sec. Decolouration |

Standard conditions/reaction conditions: (per minute)

| | |
|---|---|
| Substrate: | starch, approx. 0.17 g/L |
| Buffer: | Citrate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | Lambda = 590 nm |
| Enzyme concentration: | 0.025 AFAU/mL |
| Enzyme working range: | 0.01-0.04 AFAU/mL |

Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amg Incubation:

| | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Protease Activity (AU)

Dimethyl casein (DMC) is hydrolyzed by the proteolytic enzyme to small peptides. The primary amino groups formed in this process react with trinitrobenzene sul-phonic acid (TNBS) forming a coloured complex. This colour development is monitored in situ so the change in absorption per time unit can be calculated. This figure is a measure of the reaction rate and thus of the enzyme activity.

| Reaction conditions for the DMC reaction | |
|---|---|
| Temperature: | 50° C. |
| pH: | 8.3 |
| Wavelength: | 405 nm |
| Reaction time: | 8 min. |
| Measuring time: | 2 min. |
| Enzyme concentration range: | 0.072-0.216 mAU/ml. |

The activity is determined relative to an enzyme standard.

The assay is further described in standard method document EB-SM-0218.02/02 available upon request from Novozymes A/S, Denmark.

Relative Activity and Remaining Activity

"Relative Activity" and "Remaining Activity" is determined as described in Example 1.

Themostability

Thermostability in Example 2 is determined using the Zein-BCA assay.

EXAMPLES

Example 1

Preparation of Protease Variants and Test of Thermostability

Chemicals used were commercial products of at least reagent grade.

Strains and Plasmids:

E. coli DH12S (available from Gibco BRL) was used for yeast plasmid rescue. pJTP000 is a S. cerevisiae and E. coli shuttle vector under the control of TPI promoter, constructed from pJC039 described in WO 01/92502, in which the Thermoascus aurantiacus M35 protease gene (WO 03/048353) has been inserted.

*Saccharomyces cerevisiae* YNG318 competent cells: MATa Dpep4[cir+] ura3-52, leu2-D2, his 4-539 was used for protease variants expression. It is described in J. Biol. Chem. 272(15): 9720-9727 (1997).

Media and Substrates

10× Basal solution: Yeast nitrogen base w/o amino acids (DIFCO) 66.8 g/L, succinate 100 g/l, NaOH 60 g/l.

SC-glucose: 20% glucose (i.e., a final concentration of 2%=2 g/100 mL)) 100 mL/L, 5% threonine 4 mL/L, 1% tryptophan 10 ml/l, 20% casamino acids 25 ml/l, 10× basal solution 100 ml/l. The solution is sterilized using a filter of a pore size of 0.20 micrometer. Agar (2%) and $H_2O$ (approx. 761 mL) is autoclaved together, and the separately sterilized SC-glucose solution is added to the agar solution.

YPD: Bacto peptone 20 g/l, yeast extract 10 g/L, 20% glucose 100 mL/L.

YPD+Zn: YPD+0.25 mM $ZnSO_4$.

PEG/LiAc solution: 40% PEG4000 50 ml, 5 M Lithium Acetate 1 mL. 96 well Zein micro titre plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, NY; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endonucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Themoascus M35 protease gene was amplified with the primer pair Prot F (SEQ ID NO: 5) and Prot R (SEQ ID NO: 6). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 7) and AM35 (SEQ ID NO:8) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL $H_2O$ | 1 | 94° C. 2 min |
| 2 beads puRe Taq Ready-To-Go PCR (Amersham Biosciences) | 2 | 94° C. 30 sec |
| 0.5 microL × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 mL of 12.5% azo-casein in ethanol in 96 mL of 20 mM sodium acetate, pH 4.5, containing 0.01% triton-100 and 0.25 mM $ZnSO_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, Appl. Environ. Microbiol. 67: 4701-4707. For each of the constructs 10-20 strains were isolated, purified and cultivated in shake flasks.

Purification of Expressed Variants

1. Adjust pH of the 0.22 µm filtered fermentation sample to 4.0.
2. Put the sample on an ice bath with magnetic stirring. Add $(NH_4)_2SO_4$ in small aliquots (corresponding to approx. 2.0-2.2 M $(NH_4)_2SO_4$ not taking the volume increase into account when adding the compound).
3. After the final addition of $(NH_4)_2SO_4$, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 mL 50 mM Na-acetate pH 4.0.
6. Filter the sample by vacuum suction using a 0.22 micro m PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 mL Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100× G and 25° C.
7. 200 microL of the supernatant is transferred to a MTP, and the absorbance at 590 nm is recorded.

TABLE 1

Relative Activity of protease variants. Numbering of substitution(s) starts from N-terminal of the mature peptide in amino acids 1 to 177 of SEQ ID NO: 3.

| Variant | Substitution(s) and/or deletion(s) | Remaining Activity 80° C. | 84° C. |
|---|---|---|---|
| JTP082 | ΔS5/D79L/S87P/A112P/D142L | | 53% |
| JTP091 | D79L/S87P/A112P/T124V/D142L | 43% | |
| JTP092 | ΔS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142 L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 2

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. | 85° C./70° C. |
|---|---|---|---|
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 3

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 2

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:
1) Mix 10 microL of 10 micro g/mL enzyme solutions and 100 microL of 0.025% zein solution in a micro titer plate (MTP).
2) Incubate at various temperatures for 60 min.
3) Add 10 microL of 100% trichloroacetic acid (TCA) solution.
4) Centrifuge MTP at 3500 rpm for 5 min.
5) Take out 15 microL to a new MTP containing 100 microL of BCA assay solution (Pierce Cat #:23225, BCA Protein Assay Kit).
6) Incubate for 30 min. at 60° C.
7) Measure A562.

The results are shown in Table 4. All of the tested protease variants showed an improved thermostability as compared to the wild type (WT) protease.

Table 4 Zein-BOA Assay

| WT/Variant | Sample incubated 60 min at indicated temperatures (° C.) (micro g/mL Bovine serum albumin equivalent peptide released) | | | | | | |
|---|---|---|---|---|---|---|---|
| | 60° C. | 70° C. | 75° C. | 80° C. | 85° C. | 90° C. | 95° C. |
| WT (wild-type) | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 104 | 105 | 99 | 56 | 31 |
| JTP188 (D79L + Y82F + S87G + D104P + A112P + D142L) | 71 | 83 | 86 | 93 | 100 | 75 | 53 |
| JTP196 (A27K + D79L + Y82F + S87G + D104P + A112P + A126V + D142L) | 87 | 99 | 103 | 106 | 117 | 90 | 38 |

Example 3

Determination of Relative Activity for Proteases Using Azo Casein Assay 20 microL of samples containing approx. 0.01 mg/ml were mixed with 150 microL of substrate solution (4 mL of 12.5% azo-casein in ethanol in 96 mL of 20 mM sodium acetate, pH 4.5, containing 0.01% triton-100 and 0.25 mM ZnSO$_4$) and incubated for 5 hours at 70° C. and 80° C.

After adding 20 microL/well of 100% trichloroacetic acid (TCA) solution, the plate was centrifuge and 80 microL of supernatants were pipette out to measure A440.

| Sample name | Relative Activity 80° C./70° C. |
|---|---|
| Protease RH | 34% |
| Protease TF | 106% |
| Portease TA | 19% |
| Protease PF | 154% |

Example 4

Oil Extraction after Protease treatment of Whole Stillage

Industrially produced whole stillage collected from a first generation dry-grind corn ethanol plant (12-13% DS) was heated to 85° C., pH 4, in a water bath (Fisher Scientific IsoTemp 220) for two hours. Approximately 25 grams of whole stillage was then aliquoted into pre-weighed 50 ml conical tubes (VWR 89039-660) and incubated an additional two hours in the water bath. Enzymes were dosed according to the specifications in Table 5 and the volume of stock solution to add to fermentation was found using the equation:

$$Enz.\text{dose (ml)} = \frac{\text{Final } enz.\text{dose (mg } EP/\text{g } DS) \times \text{Mash weight(g)} \times \text{Solid content (\%} DS)}{Conc.\text{enzyme (mg } EP/\text{ml)}}$$

TABLE 5

| Enzyme doses | | |
|---|---|---|
| Enzyme | Dose | Units |
| 1 Control | 0.00 | μg ep/s DS |
| 2 PF | 20.00 | μg ep/s DS |
| 3 RH | 20.00 | μg ep/g DS |
| 4 TA | 20.00 | μg ep/g DS |
| 5 TA 196 | 20.00 | μg ep/g DS |
| 6 TF | 20.00 | μg ep/g DS |

Water was dosed into each sample such that the total added volume of enzyme and water was ~80 μL/25 g sample. Tubes were capped and placed in a hybridization rotessirie oven (Boekel Big Shot III Model #230402) set at 85° C. with rotation (setting #14) for 2 hours. After incubation, tubes were cooled to room temperature then weighed prior to oil extraction. Hexane was added to each sample at a dose of 0.125 mL hexane/1 g of whole stillage material. Each tube was covered in Dura-seal to prevent sample leakage, and mixed thoroughly. Tubes were centrifuged at 3,000×g for 10 minutes in an Avanti JE Series centrifuge with JS-5.3 rotor (Beckmann Coulter). After centrifugation, the oil/hexane layer (supernatant) was removed using a positive displacement pipette (Ranin MR-250 and MR-1000), transferred to a pre-weighed 5 mL flip-top tube (Fisherbrand 03-338-1C), and reweighed. The density of the sample was measured using a Rudolph Research Analytical density meter (DDM 2911). The density of the supernatant was then inserted into the standard curve equation derived by numerous percent oil in hexane mixtures measured on the densitometer to determine the percent oil in the supernatant.

$$\left| (\rho_o + \gamma - \rho_h)/(2^*\gamma) - sqrt((\rho_o + \gamma - \rho_h)^{\wedge}2 + 4^*\gamma^*\rho_h - 4^*\gamma^*\rho)/(2^*y) = \% \text{oil} \right.$$
$$\rho o = \text{density of oil}$$
$$\rho h = \text{density of hexane}$$
$$\gamma = \text{excess molar volume coefficient}$$

Figure 2:
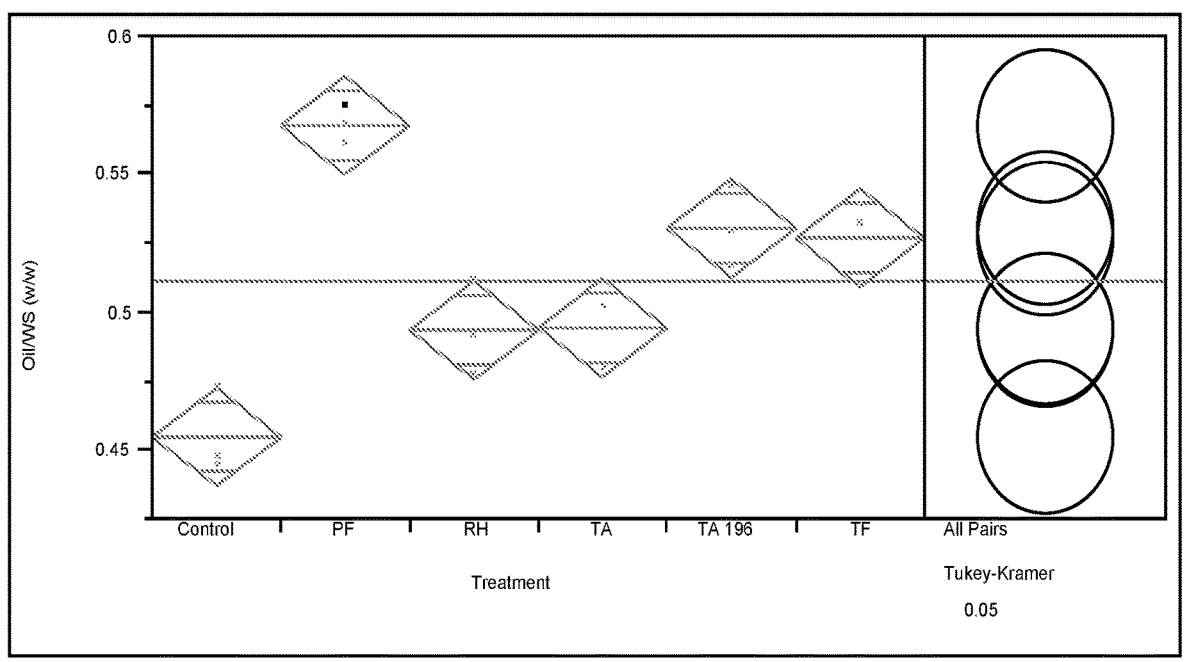
FIG. 2 shows the % oil extracted from the whole stillage for Control (No protease), Protease PF, Protease RH, Protease TA and Protease TA 196, Protease TF.

From this value the total percent oil in the starting material (whole stillage) was derived. Results are displayed in FIG. 2 (Control=no enzyme; Protease PF; Protease RH; Protease TA; Protease TA196; Protease TF).

Conclusions

Addition of proteases was found to have a positive significant impact on corn oil extraction from whole stillage. The results show a statistically higher extraction of corn oil for Protease PF, Protease TA 196, and Protease TF, 25%, 17%, and 16%, respectively, higher than the Control.

Example 5

Oil Extraction from Liquefied Corn Mash Using Protease

Four slurries were prepared by combining industrially produced ground corn and -backset from a first generation dry-grind ethanol plant and tap water to a target total weight of 180 g at 32.50% Dry Solids (DS). Initial slurry pH was approximately 5.1 and was adjusted with either 45% KOH or 40% v/v $H_2SO_4$ to pH 5.8. Enzymes were dosed according to the specifications in Table 6 and the volume of stock solution to add to fermentation was found using the equation:

$$Enz.\text{dose (ml)} = \frac{\text{Final } enz.\text{dose (mg}EP/g\,DS)\times}{\text{Slurry weight(g)}\times\text{Solid content (\%}DS)}{Conc.\text{enzyme (mg}EP/\text{ml})}$$

TABLE 6

Experimental Plan

| | Amylase | Dose | Units | Protease | Dose | Units |
|---|---|---|---|---|---|---|
| Control | LSCDS | 0.02 | % w/w corn | | | |
| 1 | LSCDS | 0.02 | % w/w corn | PF | 2.5 | µg EP/g DS |
| 2 | LSCDS | 0.02 | % w/w corn | PF | 5.0 | µg EP/g DS |

Liquefactions took place in a Labomat BFA-24 (Mathis, Concord, NC) using the following parameters: 6° C./min. Ramp, 15 minute Ramp to 80° C., hold for 1 min, Ramp to 85° C. at 1° C./min and holding for 103 min., 40 rpm for 30 seconds to the left and 30 seconds to the right. Following liquefaction, all canisters were cooled in an ice bath to room temperature then transferred to a beaker and stirred. The dry solids content of each mash was measured on a HB43-S moisture balance (Mettler-Toledo, Cleveland, Ohio). Approximately 25 grams of liquefact was then aliquoted into pre-weighed 50 ml conical tubes (VWR 89039-660). Hexane was added to each sample at a dose of 0.125 mL hexane/1 g of liquefact material. Each tube was covered in Dura-seal to prevent sample leakage, and mixed thoroughly. Tubes were centrifuged at 3,000×g for 10 minutes in an Avanti JE Series centrifuge with JS-5.3 rotor (Beckmann Coulter). After centrifugation, the oil/hexane layer (supernatant) was removed using a positive displacement pipette (Ranin MR-250 and MR-1000), transferred to a pre-weighed 5 mL flip-top tube (Fisherbrand 03-338-1C), and reweighed. The density of the sample was measured using a Rudolph Research Analytical density meter (DDM 2911). The density of the supernatant was then inserted into a standard curve equation derived by numerous percent oil in hexane mixtures measured on the densitometer to determine the percent oil in the supernatant.

$$\left| (\rho_o + \gamma - \rho_h)/(2^*\gamma) - sqrt((\rho_o + \gamma - \rho_h)^{\wedge}2 + 4^*\gamma^*\rho_h - 4^*\gamma^*\rho)/(2^*y) = \% \text{oil} \right.$$
$$\rho o = \text{density of oil}$$
$$\rho h = \text{density of hexane}$$
$$\gamma = \text{excess molar volume coefficient}$$

Figure 3:
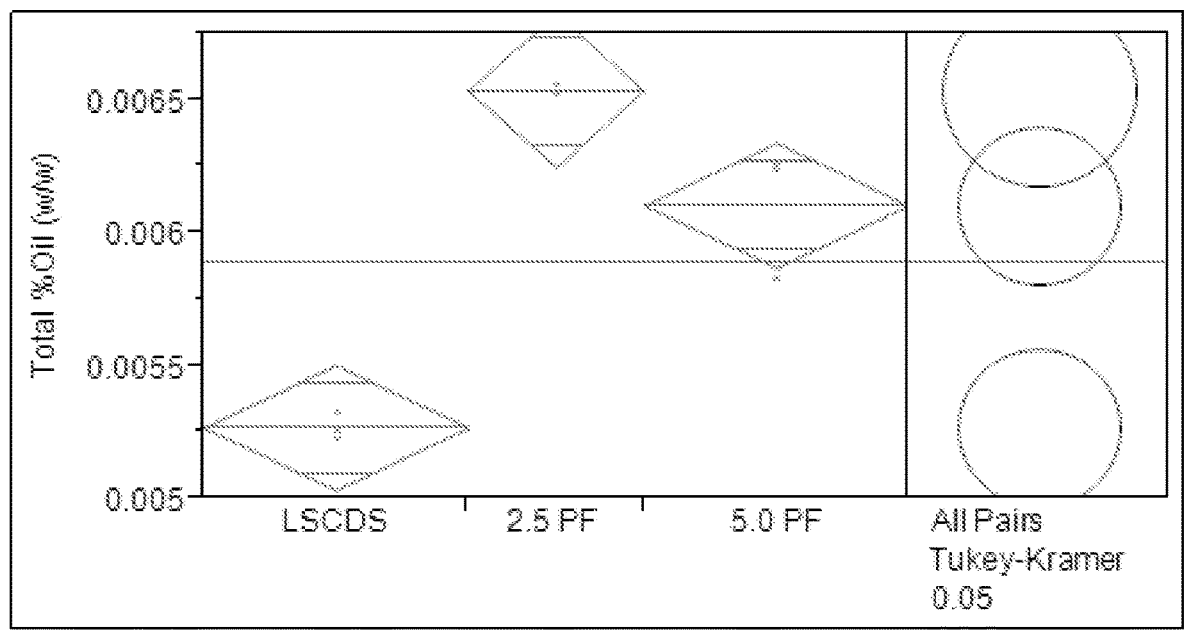
FIG. 3 shows the % oil extracted from liquefied corn mash for Control and Protease PF.

From this value the total percent oil in the starting material (liquefact) was derived. Results are displayed in FIG. 3 (Control=no enzyme; Protease PF).

Conclusions:

Addition of Protease PF was found to have a positive significant impact on corn oil extraction from liquefied material. The results show a statistically different higher extraction of corn oil for PF between 16 and 24%.

Example 6

Oil Extraction after Protease Treatment of Evaporated Centrate (Syrup)

Industrially produced syrup collected from a first generation dry-grind corn ethanol plant (8-40% DS) was heated to 85° C., pH 4, in a water bath (Fisher Scientific IsoTemp 220) for two hours. Approximately 25 grams of syrup was then aliquoted into pre-weighed 50 ml conical tubes (VWR 89039-660) and incubated an additional two hours in the water bath. Enzymes were dosed according to the specifications in Table 7 and the volume of stock solution to add to fermentation was found using the equation:

$$Enz.\text{dose (ml)} = \frac{\text{Final } enz.\text{dose (mg } EP/\text{g } DS) \times \text{Mash weight(g)} \times \text{Solid content (\%}DS)}{Conc.\text{enzyme (mg } EP/\text{ml)}}$$

TABLE 7

Enzyme doses

|   | Enzyme  | Dose  | Units      |
|---|---------|-------|------------|
| 1 | Control | 0.00  | µg ep/g DS |
| 2 | PF      | 20.00 | µg ep/g DS |
| 3 | RH      | 20.00 | µg ep/g DS |
| 4 | TA      | 20.00 | µg ep/g DS |
| 5 | TA 196  | 20.00 | µg ep/g DS |
| 6 | TF      | 20.00 | µg ep/g DS |

Figure 4:
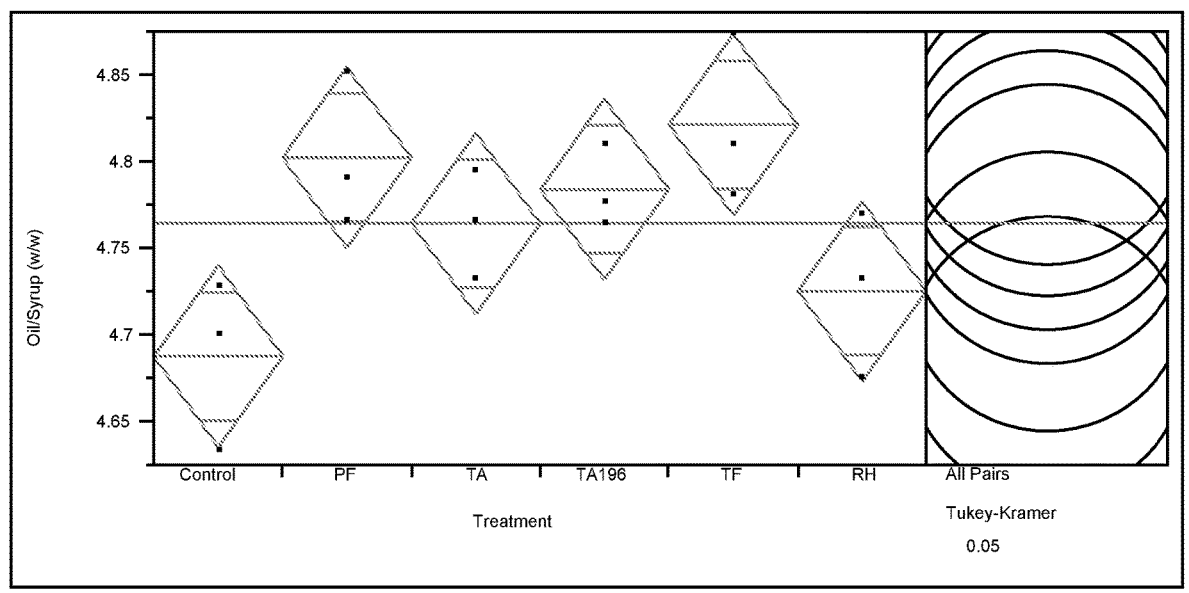
FIG. 4 shows the % oil extraction from syrup for Control (No protease), Protease PF, Protease RH, Protease TA and Protease TA 196, Protease TF.

Water was dosed into each sample such that the total added volume of enzyme and water was ~90 µL/25 g sample. Tubes were covered and placed in a water bath set at 85° C. for 2 hours with vortexing every 15 minutes. After incubation, tubes were cooled to room temperature then weighed prior to oil extraction. Hexane was added to each sample at a dose of 0.18 mL hexane/1 g of syrup material. Each tube was covered in Dura-seal to prevent sample leakage, and mixed thoroughly. Tubes were centrifuged at 3,000×g for 10 minutes in an Avanti JE Series centrifuge with JS-5.3 rotor (Beckmann Coulter). After centrifugation, the oil/hexane layer (supernatant) was removed using a positive displacement pipette (Ranin MR-250 and MR-1000), transferred to a pre-weighed 5 mL flip-top tube (Fisherbrand 03-338-1C), and reweighed. The density of the sample was measured using a Rudolph Research Analytical density meter (DDM 2911). The density of the supernatant was then inserted into the standard curve equation derived by numerous percent oil in hexane mixtures measured on the densitometer to determine the percent oil in the supernatant.

$$\left| (\rho_o + \gamma - \rho_h)/(2^*\gamma) - sqrt\big((\rho_o + \gamma - \rho_h)^\wedge 2 + 4^*\gamma^*\rho_h - 4^*\gamma^*\rho\big)\big/(2^*y) = \% \text{ oil} \right|$$
Where $\rho$ is the measured density From this value the total percent oil in the starting material (syrup) was derived. Results are displayed in FIG. 4 (Control=no enzyme; Protease PF; Protease RH; Protease TA; Protease TA196; Protease TF).

Conclusions

Addition of proteases was found to have a positive significant impact on corn oil extraction from syrup. The results show a statistically higher extraction of corn oil for Protease TF, and Protease PF, 2.9%, and 2.4%, respectively, higher than the Control.

Example 7

Oil Extraction from Liquefied Corn Mash Using Protease

Eighteen slurries were prepared by combining industrially produced ground corn and backset from a first generation dry-grind ethanol plant and tap water to a target total weight of 30 g at 32.50% Dry Solids (DS). Initial slurry pH was approximately 5.1 and not adjusted. Enzymes were dosed according to the specifications in Table 8 and the volume of stock solution to add to fermentation was found using the equation:

$$Enz.\text{dose (ml)} = \frac{\text{Final } enz.\text{dose (mg } EP/\text{g } DS) \times \text{Slurry weight(g)} \times \text{Solid content (\%}DS)}{Conc.\text{enzyme (mg } EP/\text{ml)}}$$

Water was dosed into each sample such that the total added volume of enzyme and water was approx. 230 µL/30 g sample. Tubes were covered with a strip of Dura-seal, capped and placed in a water bath set at 85° C. for 2 hours with vortexing every 15 minutes. After incubation, tubes were cooled in a room temperature water bath for 15 minutes then weighed prior to oil extraction. Hexane was added to each sample at a dose of 0.125 mL hexane/1 g of liquefied material. Each tube was covered in Dura-seal to prevent sample leakage, and mixed thoroughly. Tubes were centrifuged at 3,000×g for 10 minutes in an Avanti JE Series centrifuge with JS-5.3 rotor (Beckmann Coulter). After centrifugation, the oil/hexane layer (supernatant) was removed using a positive displacement pipette (Ranin MR-250 and MR-1000), transferred to a pre-weighed 5 mL flip-top tube (Fisherbrand 03-338-1C), and reweighed. The density of the sample was measured using a Rudolph Research Analytical density meter (DDM 2911). The density of the supernatant was then inserted into a standard curve equation derived by numerous percent oil in hexane mixtures measured on the densitometer to determine the percent oil in the supernatant.

$$\left| \begin{array}{c} (\rho_o + \gamma - \rho_h)/(2^*\gamma) - sqrt\big((\rho_o + \gamma - \rho_h)^\wedge 2 + 4^*\gamma^*\rho_h - 4^*\gamma^*\rho\big)\big/(2^*y) = \% \text{ oil} \\ \rho o = \text{density of oil} \\ \rho h = \text{density of hexane} \\ \gamma = \text{excess molar volume coefficient} \end{array} \right|$$

Figure 5:
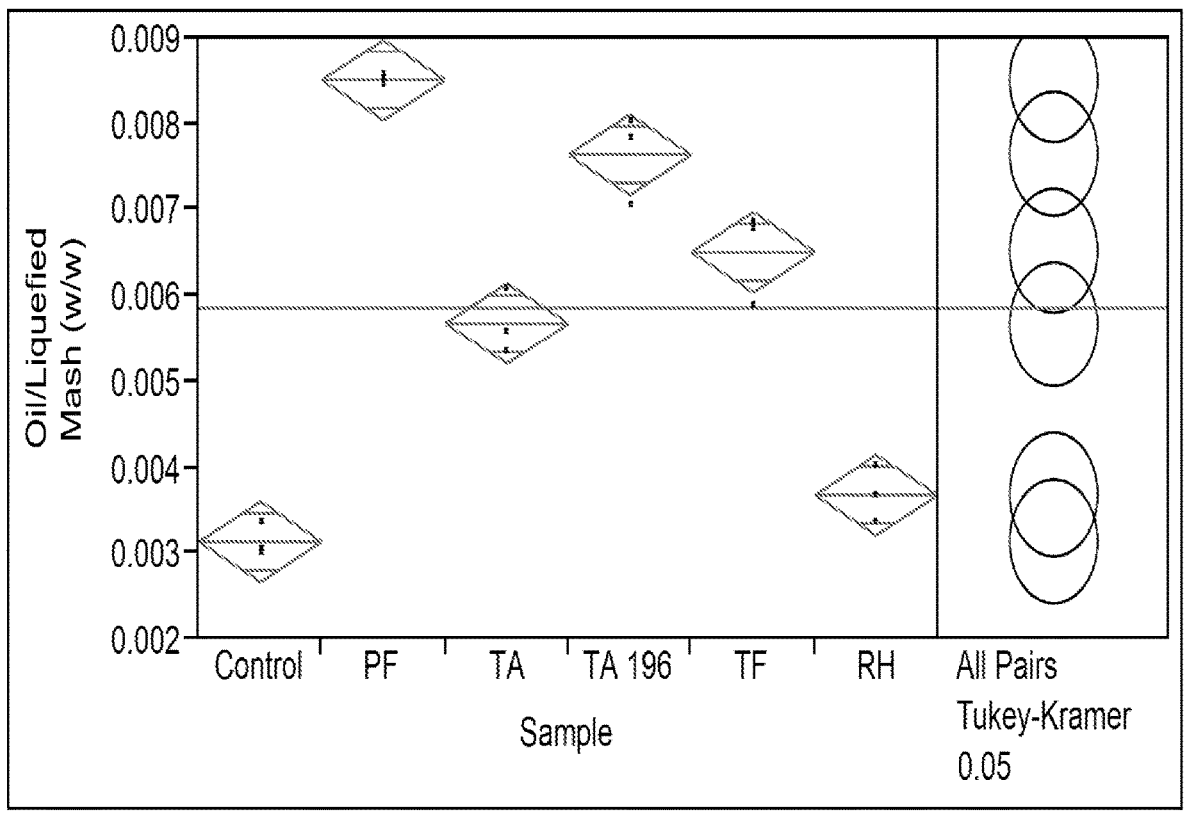
FIG. 5 shows % oil in the liquefied corn mash (liquefact) for Control (No Protease), Protease PF, Protease RH, Protease TA, Protease TA196 and Protease TF.

From this value the total % oil in the starting material (liquefact) was derived. Results are displayed in FIG. 5 (Control=no enzyme; Protease PF; Protease RH; Protease TA; Protease TA196; Protease TF).

TABLE 8

Experimental Plan

| | Alpha-Amylase | Dose | Units | Protease | Dose | Units |
|---|---|---|---|---|---|---|
| Control | 369 | 0.02 | % w/w corn | | 0 | μg EP/g DS |
| Control | 369 | 0.02 | % w/w corn | | 0 | μg EP/g DS |
| Control | 369 | 0.02 | % w/w corn | | 0 | μg EP/g DS |
| 1 | 369 | 0.02 | % w/w corn | PF | 20 | μg EP/g DS |
| 2 | 369 | 0.02 | % w/w corn | PF | 20 | μg EP/g DS |
| 3 | 369 | 0.02 | % w/w corn | PF | 20 | μg EP/g DS |
| 4 | 369 | 0.02 | % w/w corn | TA | 20 | μg EP/g DS |
| 5 | 369 | 0.02 | % w/w corn | TA | 20 | μg EP/g DS |
| 6 | 369 | 0.02 | % w/w corn | TA | 20 | μg EP/g DS |
| 7 | 369 | 0.02 | % w/w corn | TA 196 | 20 | μg EP/g DS |
| 8 | 369 | 0.02 | % w/w corn | TA 196 | 20 | μg EP/g DS |
| 9 | 369 | 0.02 | % w/w corn | TA 196 | 20 | μg EP/g DS |
| 10 | 369 | 0.02 | % w/w corn | TF | 20 | μg EP/g DS |
| 11 | 369 | 0.02 | % w/w corn | TF | 20 | μg EP/g DS |
| 12 | 369 | 0.02 | % w/w corn | TF | 20 | μg EP/g DS |
| 13 | 369 | 0.02 | % w/w corn | RH | 20 | μg EP/g DS |
| 14 | 369 | 0.02 | % w/w corn | RH | 20 | μg EP/g DS |
| 15 | 369 | 0.02 | % w/w corn | RH | 20 | μg EP/g DS |

Conclusions

Addition of protease was found to have a positive significant impact on corn oil extraction from liquefied mash. The results show a statistically higher extraction of corn oil for Protease PF, Protease TA196, Protease TF and Protease TA, 171.1%, 143.4%, 107.3%, and 80.9%, respectively, higher than the Control.

The present invention is further described in the following numbered paragraphs:

1. A process of recovering oil, comprising
   (a) converting a starch-containing material into dextrins with an alpha-amylase; optionally recovering oil during and/or after step (a)
   (b) saccharifying the dextrins using a carbohydrate source generating enzyme to form a sugar;
   (c) fermenting the sugar in a fermentation medium into a fermentation product using a fermenting organism;
   (d) recovering the fermentation product to form a whole stillage;
   (e) separating the whole stillage into thin stillage and wet cake;
   (e') optionally concentrating the thin stillage into syrup;
   (f) recovering oil from the thin stillage and/or optionally the syrup, wherein a protease having a thermostability value of more than 20% determined as Relative Activity at 80° C./70° C. is present and/or added during step (a) or steps (d)-(e').

2. The process of paragraph 1, wherein the protease is present in and/or added in starch-containing material converting step (a).

3. The process of paragraphs 1-2, wherein saccharification step b) and fermentation step c) are carried out simultaneously or sequentially.

4. The process of any of paragraphs 1-3, wherein starch-containing material is converted to dextrins by liquefaction.

5. The process of any of paragraphs 1-4, wherein the temperature in step (a) is above the initial gelatinization temperature, such as at a temperature between 80-90° C., such as around 85° C.

6. The process of paragraphs 4-5, wherein a jet-cooking step is carried out before in step (a).

7. The process of paragraph 6, wherein jet-cooking is carried out at a temperature between 95-140° C. for about 1-15 minutes, preferably for about 3-10 minutes, especially around about 5 minutes.

8. The process of any of paragraphs 1-7, wherein the pH in step (a) is from 4-7, preferably 4.5-6.

9. The process of any of paragraphs 1-8, further comprising, before step (a), the steps of: i) reducing the particle size of the starch-containing material, preferably by dry milling; ii) forming a slurry comprising the starch-containing material and water.

10. The process of any of paragraphs 1-9, further comprising a pre-saccharification step, before saccharification step (b), carried out for 40-90 minutes at a temperature between 30-65° C.

11. The process of any of paragraphs 1-10, wherein saccharification is carried out at a temperature from 20-75° C., preferably from 40-70° C., such as around 60° C., and at a pH between 4 and 5.

12. The process of any of paragraphs 1-11, wherein fermentation step (c) or simultaneous saccharification and fermentation (SSF) (i.e., steps (b) and (c)) are carried out at a temperature from 25° C. to 40° C., such as from 28° C. to 35° C., such as from 30° C. to 34° C., preferably around about 32° C.

13. The process of any of paragraphs 1-12, wherein fermentation step (c) or simultaneous saccharification and fermentation (SSF) (i.e., steps (b) and (c)) are ongoing for 6 to 120 hours, in particular 24 to 96 hours.

14. The process of any of paragraphs 1-13, wherein starch-containing material converting step (a), saccharification step (b) and fermentation step (c) are carried out simultaneously or sequentially.

15. The process of paragraph 14, wherein starch-containing material converting step (a) is carried out at a temperature below the initial gelatinization temperature, preferably from 20-60° C., such as 25-40° C., such as around 30-35° C., such as around 32° C.

16. The process of paragraph 15, wherein the starch-containing material is converted to dextrins and the dextrins are saccharified to a sugar by treating the starch-containing material with an alpha-amylase and glucoamylase below the initial gelatinization temperature of the starch-containing material.

17. The process of any of paragraphs 15 or 16, wherein the conversion of the starch-containing material to dextrins, the saccharification of the dextrins to sugars, and the fermentation of the sugars are carried out in a single step.

18. The process of any of paragraphs 14-17, wherein the glucoamylase is derived from a strain of *Trametes*, such as a strain of *Trametes cingulata*, or a strain of *Athelia*, such as a strain of *Athelia rolfsii*.

19. The process of any of paragraphs 14-18, wherein the alpha-amylase is derived from a strain *Rhizomucor*, such as a strain of *Rhizomucor pusillus*, such as a *Rhizomucor pusillus* alpha-amylase with a starch-binding domain (SBD), such as a *Rhizomucor pusillus* alpha-amylase with *Aspergillus niger* glucoamylase linker and SBD.

20. The process of any of paragraphs 14-19, wherein the starch-containing material is granular starch.

21. The process of any of paragraphs 14-20, wherein the starch-containing material is reducing the particle size, preferably by milling, to 0.05 to 3.0 mm, preferably 0.1-0.5 mm.

22. The process of any of paragraphs 14-21, wherein simultaneous saccharification and fermentation (SSF) is carried out so that the sugar level, such as glucose level, is kept below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%.

23. The process of any of paragraphs 14-22, wherein the pH in is from 4-7, preferably 4.5-6 when conversion of the starch-containing material to dextrins, the saccharification of the dextrins to a sugar, and the fermentation of the sugar are carried out in a single step.

24. The process of any of paragraphs 1-23, wherein starch-containing material in step (a), including granular starch, contains 20-55 wt.-% dry solids, preferably 25-40 wt.-% dry solids, more preferably 30-35% dry solids.

25. The process of any of paragraphs 1-24, wherein the protease is present in and/or added to the whole stillage in step (d) and/or the thin stillage in or after separation in step (e), and/or syrup in step (e').

26. The process of any of paragraphs 1-25, wherein separation in step (e) is carried out by centrifugation, preferably a decanter centrifuge, filtration, preferably using a filter press, a screw press, a plate-and-frame press, a gravity thickener or decker.

27. The process of any of paragraphs 1-26, wherein the starch-containing material is cereal.

28. The process of any of paragraphs 1-27, wherein the starch-containing material is selected from the group consisting of corn, wheat, barley, cassava, sorghum, rye, potato, beans, milo, peas, rice, sago, sweet potatoes, tapioca, or any combination thereof.

29. The process of any of paragraphs 1-28, wherein the fermentation product is selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones.

30. The process of any of paragraphs 1-29, wherein the fermentation product is ethanol.

31. The process of any of paragraphs 1-30, wherein the carbohydrate source generating enzyme in step (b) is a glucoamylase.

32. The process of any of paragraphs 1-31, wherein the glucoamylase present and/or added during saccharification and/or fermentation is of fungal origin, preferably from a strain of *Aspergillus*, preferably *A. niger, A. awamori*, or *A. oryzae*; or a strain of *Trichoderma*, preferably *Trichoderma reesei*; or a strain of *Talaromyces*, preferably *Talaromyces emersonii*, or a strain of *Pycnoporus*, or a strain of *Gloeophyllum*.

33. The process of any of paragraphs 1-32, wherein the fermentation product is recovered by distillation.

34. The process of recovering oil of any of paragraphs 1-33, comprising
(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease having a thermostability value of more than 20% determined as Relative Activity at 80° C./70° C. is present and/or added during step (a) or any of paragraphs (d)-(e').

35. The process of paragraph 34, wherein the temperature during step (a) is between 80-90° C., such as around 85° C.

36. The process of recovering oil of any of paragraphs 1-35, comprising
(a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease having a thermostability value of more than 20% determined as Relative Activity at 80° C./70° C. is present and/or added during any of step (d)-(e').

37. The process of paragraph 36, wherein the temperature during step (a) is from 25° C. to 40° C., such as from 28° C. to 35° C., such as from 30° C. to 34° C., preferably around about 32° C.

38. The process of any of paragraphs 1-37, wherein the oil is recovered from the thin stillage and/or syrup/evaporated centrate, e.g., by extraction, such as hexane extraction.

39. The process of any of paragraphs 1-38, wherein the protease has a thermostability of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

40. The process of any of paragraphs 1-39, wherein the protease has a thermostability between 50 and 115%, such as between 50 and 70%, such as between 50 and 60%, such as between 100 and 120%, such as between 105 and 115% determined as Relative Activity at 80° C./70° C.

41. The process of any of paragraphs 1-40, wherein the protease has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

42. The process of any of paragraphs 1-41, wherein the protease has a thermostability between 10 and 50%, such as between 10 and 30%, such as between 10 and 25% determined as Relative Activity at 85° C./70° C.

43. The process of any of paragraphs 1-42, wherein the protease has a thermostability between 50 and 110%, such as between 70 and 110%, such as between 90 and 110% determined as Relative Activity at 85° C./70° C.

44. The process of any of paragraphs 1-43, wherein the protease is of fungal origin.

45. The process of any of paragraphs 1-44, wherein the protease is a variant of the metallo protease derived from a strain of the genus *Thermoascus*, preferably a strain of *Thermoascus aurantiacus*, especially *Thermoascus aurantiacus* CGMCC No. 0670.

46. The process of any of paragraphs 1-45, wherein the protease is a variant of the metallo protease disclosed as the mature part of SEQ ID NO: 2 disclosed in WO 2003/048353 or SEQ ID NO: 3 herein.

47. The process of any of paragraphs 1-46, wherein the parent protease has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as least 100% identity to the mature part of the polypeptide of SEQ ID NO: 2 disclosed in WO 2003/048353 or SEQ ID NO: 3 herein.

48. The process of any of paragraphs 1-47, wherein the protease variant has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or SEQ ID NO: 3 herein.

49. The process of any of paragraphs 1-48, wherein the protease is a variant of the *Thermoascus aurantiacus* protease shown in SEQ ID NO: 3 herein with the mutations selected from the group consisting of:
   A27K+D79L+Y82F+S87G+D104P+A112P+A126V+D142L;
   D79L+Y82F+S87G+A112P+D142L;
   Y82F+S87G+S70V+D79L+D104P+A112P+D142L;
   Y82F+S87G+D79L+D104P+A112P+A126V+D142L.

50. The process of any of paragraphs 1-49, wherein the protease is derived from *Rhizomucor*, such as *Rhizomucor miehei*, such as the protease shown in SEQ ID NO: 9 or one having a sequence identity thereto of at least 60%, at least 70%, at least 80%, at least 90%, at least 95%, at least 96%, at least 97%, at least 98%, at least 99%.

51. The process of any of paragraphs 1-50, wherein the protease is added in a concentration of 0.01-100, such 0.1-10 micro g/g DS.

52. The process of any of paragraphs 1-51, wherein the protease is of bacterial origin.

53. The process of any of paragraphs 1-52, wherein the protease is derived from a strain of *Pyrococcus*, preferably a strain of *Pyrococcus furiosus*.

54. The process of any of paragraphs 1-53, wherein the protease is the one shown in SEQ ID NO: 1 in U.S. Pat. No. 6,258,726 or SEQ ID NO: 4 herein.

55. The process of any of paragraphs 1-54, wherein the protease has at least 60%, such as at 30 least 70%, such as at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 4 herein.

56. The process of any of paragraphs 1-54, wherein the protease is a bacterial serine protease, such as derived from a strain of *Thermobifida*, such as *Thermobifida fusca*, such as the protease shown in SEQ ID NO: 10 or one having a sequence identity thereto of at least 60%, at least 70%, at least 80%, at least 90%, at least 95%, at least 96%, at least 97%, at least 98%, at least 99%.

57. The process of any of paragraphs 1-56, wherein the alpha-amylase in step (a) is a bacterial alpha-amylase.

58. The process of any of paragraphs 1-57, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular the *Bacillus stearothermophilus* alpha-amylase is truncated, preferably to have from 485-495 amino acids, such as around 491 amino acids.

59. The process of any of paragraphs 1-58, wherein the alpha-amylase is selected from the group of *Bacillus stearothermophilus* alpha-amylase variants comprising a double deletion, such as I181*+G182*, or I181*+G182*+N193F (using SEQ ID NO: 1 for numbering).

60. The process of any of paragraphs 1-59, wherein the alpha-amylase is selected from the group of *Bacillus stearothermophilus* alpha-amylase variants:
   I181*+G182*+N193F+E129V+K177L+R179E;
   181*+G182*+N193F+V59A+Q89R+E129V+K177L+R179E+H208Y+K220P+N224L+Q254S;
   I181*+G182*+N193F+V59A  Q89R+E129V+K177L+R179E+Q254S+M284V; and
   I181*+G182*+N193F+E129V+K177L+R179E+K220P+N224L+S242Q+Q254S (using SEQ ID NO: 1 for numbering).

61. The process of any of paragraphs 1-60 wherein oil is extracted/recovered from the liquefied starch-containing material during and/or after step (a), before saccharification in step (b).

62. The process of recovering oil of any of paragraphs 1-61, comprising
   (c) converting a starch-containing material into dextrins with an alpha-amylase;
   recovering oil during and/or after step (a)
   (b) saccharifying the dextrins using a carbohydrate source generating enzyme to form a sugar;
   (c) fermenting the sugar in a fermentation medium into a fermentation product using a fermenting organism; wherein a protease having a thermostability value of more than 20% determined as Relative Activity at 80° C./70° C. is present and/or added in step (a).

62. The process of recovering oil of any of paragraphs 1-61, comprising
   (a) converting a starch-containing material into dextrins with an alpha-amylase;
   (b) saccharifying the dextrins using a carbohydrate source generating enzyme to form a sugar;
   (c) fermenting the sugar in a fermentation medium into a fermentation product using a fermenting organism;
   (d) recovering the fermentation product to form a whole stillage;
   (e) separating the whole stillage into thin stillage and wet cake;
   (e') concentrating the thin stillage into syrup;
   (f) recovering oil from the syrup, wherein a protease having a thermostability value of more than 20% determined as Relative Activity at 80° C./70° C. is present and/or added in step (e').

63. The process of paragraph 62, wherein the protease is derived from a strain of *Pyrococcus*, preferably a strain of *Pyrococcus furiosus*.

64. The process of any of paragraphs 62 or 63, wherein the protease is the one shown in SEQ ID NO: 1 in U.S. Pat. No. 6,258,726 or SEQ ID NO: 4 herein.

65. The process of any of paragraphs 62-64, wherein the protease has at least 60%, such as at least 70%, such as at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 4 herein.

66. The process of paragraph 62, wherein the protease is a bacterial serine protease, such as derived from a strain of *Thermobifida*, such as *Thermobifida fusca*, such as the protease shown in SEQ ID NO: 10 or one having a sequence identity thereto of at least 60%, at least 70%, at least 80%, at least 90%, at least 95%, at least 96%, at least 97%, at least 98%, at least 99%.

67. The process of paragraph 62, wherein the protease is of fungal origin.

68. The process of any of paragraphs 62-67, wherein the protease is a variant of the metallo protease derived from a strain of the genus *Thermoascus*, preferably a strain of *Thermoascus aurantiacus*, especially *Thermoascus aurantiacus* CGMCC No. 0670.

69. The process of any of paragraphs 62-68, wherein the protease is a variant of the metallo protease disclosed as the mature part of SEQ ID NO: 2 disclosed in WO 2003/048353 or SEQ ID NO: 3 herein.

70. The process of any of paragraphs 62-69, wherein the parent protease has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as least 100% identity to the mature part of the polypeptide of SEQ ID NO: 2 disclosed in WO 2003/048353 or SEQ ID NO: 3 herein.

71. The process of any of paragraphs 62-70, wherein the protease variant has at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or SEQ ID NO: 3 herein.

72. The process of any of paragraphs 62-71, wherein the protease is a variant of the *Thermoascus aurantiacus* protease shown in SEQ ID NO: 3 herein with the mutations selected from the group consisting of:
A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L.

73. The process of any of paragraphs 62-72, wherein the protease is derived from *Rhizo mucor*, such as *Rhizomucor miehei*, such as the protease shown in SEQ ID NO: 9 or one having a sequence identity thereto of at least 60%, at least 70%, at least 80%, at least 90%, at least 95%, at least 96%, at least 97%, at least 98%, at least 99%.

74. The process of any of paragraphs 62-73, wherein the protease is added in a concentration of 0.01-100, such 0.1-10 micro g/g DS.

75. A process of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) optionally recovering the fermentation product to form a whole stillage;
(e) optimally separating the whole stillage into thin stillage and wet cake;
(e') optionally concentrating the thin stillage into syrup;
wherein a protease having a thermostability value of more than 20% determined as Relative Activity at 80° C./70° C. is present and/or added in step (a) and/or steps (d)-(e') and oil is recovered during and/or after step (a).

76. A process of recovering oil, comprising
(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product;
wherein a protease having a thermostability value of more than 20% determined as Relative Activity at 80° C./70° C. is present and/or added in step (a) and oil is recovered during and/or after step (a).

77. A process of recovering oil, comprising
(a) converting a starch-containing material into dextrins with an alpha-amylase and *Pyrococcus furiosus* protease;
(b) saccharifying the dextrins using a carbohydrate source generating enzyme to form a sugar;
(c) fermenting the sugar in a fermentation medium into a fermentation product using a fermenting organism;
(d) recovering the fermentation product, wherein oil is recovered during and/or after step (a).

78. Use of a protease having a thermostability value of more than 20%, such as more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. for increasing oil recovery yields from thin stillage and/or syrup/evaporated centrate in a fermentation product production process.

SEQUENCE LISTING

```
Sequence total quantity: 10
SEQ ID NO: 1            moltype = AA  length = 515
FEATURE                 Location/Qualifiers
REGION                  1..515
                        note = 1..515
source                  1..515
                        mol_type = protein
                        organism = Bacillus stearothermophilus
SEQUENCE: 1
AAPFNGTMMQ YFEWYLPDDG TLWTKVANEA NNLSSLGITA LWLPPAYKGT SRSDVGYGVY    60
DLYDLGEFNQ KGTVRTKYGT KAQYLQAIQA AHAAGMQVYA DVVFDHKGGA DGTEWVDAVE   120
```

```
VNPSDRNQEI SGTYQIQAWT KFDFPGRGNT YSSFKWRWYH FDGVDWDESR KLSRIYKFRG    180
IGKAWDWEVD TENGNYDYLM YADLDMDHPE VVTELKNWGK WYVNTTNIDG FRLDAVKHIK    240
FSFFPDWLSY VRSQTGKPLF TVGEYWSYDI NKLHNYITKT NGTMSLFDAP LHNKFYTASK    300
SGGAFDMRTL MTNTLMKDQP TLAVTFVDNH DTEPGQALQS WVDPWFKPLA YAFILTRQEG    360
YPCVFYGDYY GIPQYNIPSL KSKIDPLLIA RRDYAYGTQH DYLDHSDIIG WTREGVTEKP    420
GSGLAALITD GPGGSKWMYV GKQHAGKVFY DLTGNRSDTV TINSDGWGEF KVNGGSVSVW    480
VPRKTTVSTI ARPITTRPWT GEFVRWTEPR LVAWP                              515

SEQ ID NO: 2            moltype = DNA  length = 1068
FEATURE                 Location/Qualifiers
sig_peptide             1..57
misc_feature            58..534
mat_peptide             535..1068
source                  1..1068
                        mol_type = other DNA
                        organism = Thermoascus aurantiacus
CDS                     1..1065
SEQUENCE: 2
atgcggctcg ttgcttccct aacggccttg gtggccttgt ccgtacctgt cttccccgct    60
gctgtcaacg tgaagcgtgc ttcgtcctac ctggagatca ctctgagcca ggtcagcaac   120
actctgatca aggccgtggt ccagaacact ggtagcgacg agttgtcctt cgttcacctg   180
aacttcttca aggaccccgc tcctgtcaaa aaggtatcgg tgggtctgaa                240
gtgcagttcg agggcatttt gagccgctac aaatcgactg gcctctctcg tgacgccttt   300
acttatctgg ctcccggaga gtccgtcgag gactttttg atattgcttc gacttacgat    360
ctgaccagcg gcggccctgt aactatccgt actgagggag ttgttcccta cgccacggct   420
aacagactg atattgccgg ctacatctca tactcgtcca atgtgttgac cattgatgtc    480
gatggcgccg ctgctgccac tgtctccaag gcaatcactc ctttggaccg ccgcactagg   540
atcagttcct gctccggcag cagacagagc gctcttacta cggctctcag aaacgctgct   600
tctcttgcca acgcagctgc cgacgcggct cagtctggat cagcttcaaa gttcagcgag   660
tacttcaaga ctacttctag ctctacccgc cagaccgtgg ctgcgcgtct tcgggctgtt   720
gcgcgggagg catcttcgtc ttcttcggga gccaccacgt actactgcga cgatccctac   780
ggctactgtt cctccaacgt cctggcttac accctgcctt catacaacat aatcgccaac   840
tgtgacattt tctatactta cctgccggct ctgaccagta cctgtcacgc tcaggatcaa   900
gcgaccactg cccttcacga gttcacccat gcgcctggcg tctacagccc tggcacggac   960
gacctggcgt atggctacca ggctgcgatg ggtctgcagc gcagccaggc tgtcatgaac  1020
gctgacacct acgctctcta tgcgaatgcc atataccttg gttgctaa                1068

SEQ ID NO: 3            moltype = AA   length = 355
FEATURE                 Location/Qualifiers
source                  1..355
                        mol_type = protein
                        organism = Thermoascus aurantiacus
SEQUENCE: 3
MRLVASLTAL VALSVPVFPA AVNVKRASSY LEITLSQVSN TLIKAVVQNT GSDELSFVHL    60
NFFKDPAPVK KVSVYRDGSE VQFEGILSRY KSTGLSRDAF TYLAPGESVE DVFDIASTYD   120
LTSGGPVTIR TEGVVPYATA NSTDIAGYIS YSSNVLTIDV DGAAAATVSK AITPLDRRTR   180
ISSCSGSRQS ALTTALRNAA SLANAAADAA QSGSASKFSE YFKTTSSSTR QTVAARLRAV   240
AREASSSSSG ATTYYCDDPY GYCSSNVLAY TLPSYNIIAN CDIFYTYLPA LTSTCHAQDQ   300
ATTALHEFTH APGVYSPGTD DLAYGYQAAM GLSSSQAVMN ADTYALYANA IYLGC         355

SEQ ID NO: 4            moltype = AA   length = 412
FEATURE                 Location/Qualifiers
REGION                  1..412
                        note = mat_peptide - Pyrococcus furiosus protease (Pfu)
source                  1..412
                        mol_type = protein
                        organism = Pyrococcus furiosus
SEQUENCE: 4
AELEGLDESA AQVMATYVWN LGYDSGITI GIIDTGIDAS HPDLQGKVIG WVDFVNGRSY     60
PYDDHGHGTH VASIAAGTGA ASNGKYKGMA PGAKLAGIKV LGADGSGSIS TIIKGVEWAV   120
DNKDKYGIKV INLSLGSSQS SDGTDALSQA VNAAWDAGLV VVVAAGNSGP NKYTIGSPAA   180
ASKVITGAV DKYDVITSFS SRGPTADGRL KPEVVAPGNW IIAARASGTS MGQPINDYYT   240
AAPGTSMATP HVAGIAALLL QAHPSWTPDK VKTALIETAD IVKPDEIADI AYGAGRVNAY   300
KAINYDNYAK LVFTGYVANK GSQTHQFVIS GASFVTATLY WDNANSDLDL YLYDPNGNQV   360
DYSYTAYYGF EKVGYYNPTD GTWTIKVVSY SGSANYQVDV VSDGSLSQPG SS           412

SEQ ID NO: 5            moltype = DNA  length = 49
FEATURE                 Location/Qualifiers
misc_feature            1..49
                        note = Primer
source                  1..49
                        mol_type = other DNA
                        organism = synthetic construct
SEQUENCE: 5
aacgacggta cccggggatc ggatccatgc ggctcgttgc ttccctaac                 49

SEQ ID NO: 6            moltype = DNA  length = 48
FEATURE                 Location/Qualifiers
misc_feature            1..48
```

```
                         note = Primer
source                   1..48
                         mol_type = other DNA
                         organism = synthetic construct
SEQUENCE: 6
ctaattacat gatgcggccc ttaattaatt agcaaccaag gtatatgg              48

SEQ ID NO: 7             moltype = DNA  length = 20
FEATURE                  Location/Qualifiers
misc_feature             1..20
                         note = Primer
source                   1..20
                         mol_type = other DNA
                         organism = synthetic construct
SEQUENCE: 7
taggagttta gtgaacttgc                                             20

SEQ ID NO: 8             moltype = DNA  length = 18
FEATURE                  Location/Qualifiers
misc_feature             1..18
                         note = Primer
source                   1..18
                         mol_type = other DNA
                         organism = synthetic construct
SEQUENCE: 8
ttcgagcgtc ccaaaacc                                               18

SEQ ID NO: 9             moltype = AA  length = 430
FEATURE                  Location/Qualifiers
SIGNAL                   1..22
REGION                   33..430
                         note = 33..430
source                   1..430
                         mol_type = protein
                         organism = Rhizomucor miehei
SEQUENCE: 9
MLFSQITSAI LLTAASLSLT TARPVSKQSE SKDKLLALPL TSVSRKFSQT KFGQQQLAEK   60
LAGLKPFSEA AADGSVDTPG YYDFDLEEYA IPVSIGTPGQ DFLLLFDTGS SDTWVPHKGC  120
TKSEGCVGSR FFDPSASSTF KATNYNLNIT YGTGGANGLY FEDSIAIGDI TVTKQILAYV  180
DNVRGPTAEQ SPNADIFLDG LFGAAYPDNT AMEAEYGSTY NTVHVNLYKQ GLISSPLFSV  240
YMNTNSGTGE VVFGGVNNTL LGGDIAYTDV MSRYGGYYFW DAPVTGITVD GSAAVRFSRP  300
QAFTIDTGTN FFIMPSSAAS KIVKAALPDA TETQQGWVVP CASYQNSKST ISIVMQKSGS  360
SSDTIEISVP VSKMLLPVDQ SNETCMFIIL PDGGNQYIVG NLFLRFFVNV YDFGNNRIGF  420
APLASAYENE                                                       430

SEQ ID NO: 10            moltype = AA  length = 368
FEATURE                  Location/Qualifiers
SIGNAL                   1..32
REGION                   33..368
                         note = 33..368
source                   1..368
                         mol_type = protein
                         organism = Thermobifida fusca
SEQUENCE: 10
MNHSSRRTTS LLFTAALAAT ALVAATTPAS AQELALKRDL GLSDAEVAEL RAAEAEAVEL   60
EEELRDSLGS DFGGVYLDAD TTEITVAVTD PAAVSRVDAD DVTVDVVDFG ETALNDFVAS  120
LNAIADTADP KVTGWYTDLE SDAVVITTLR GGTPAAEELA ERAGLDERAV RIVEEDEEPQ  180
SLAAIIGGNP YYFGNYRCSI GFSVRQGSQT GFATAGHCGS TGTRVSSPSG TVAGSYFPGR  240
DMGWVRITSA DTVTPLVNRY NGGTVTVTGS QEAATGSSVC RSGATTGWRC GTIQSKNQTV  300
RYAEGTVTGL TRTTACAEGG DSGGPWLTGS QAQGVTSGGT GDCRSGGITF FQPINPLLSY  360
FGLQLVTG                                                         368
```

The invention claimed is:

1. A process of recovering oil, comprising:
   (a) liquefying a starch-containing material into dextrins with a bacterial alpha-amylase at a temperature above the initial gelatinization temperature, wherein the starch-containing material comprises corn;
   (b) saccharifying the dextrins using a glucoamylase to form a sugar;
   (c) fermenting the sugar in a fermentation medium into ethanol using a yeast fermenting organism;
   (d) recovering the fermentation product to form a whole stillage;
   (e) separating the whole stillage into thin stillage and wet cake;
   (e') optionally concentrating the thin stillage into syrup; and
   (f) recovering oil from the thin stillage and/or optionally the syrup, wherein a protease having at least 60% sequence identity to the amino acid sequence of SEQ ID NO: 4 is added during step (a).

2. The process of claim 1, wherein the oil is recovered during and/or after step (a).

3. The process of claim 2, wherein oil recovery is increased higher than control.

4. The process of claim 1, wherein the oil is recovered from the thin stillage.

5. The process of claim 4, wherein oil recovery is increased higher than control.

6. The process of claim 1, wherein the oil is optionally recovered from the syrup.

7. The process of claim 6, wherein oil recovery is increased higher than control.

8. The process of claim 1, wherein the bacterial alpha-amylase is the *Bacillus stearothermophilus* alpha-amylase having the sequence of SEQ ID NO: 1 herein, which is truncated to have from 485-495 amino acids, or one having at least 70% sequence identity thereto.

9. A process of recovering oil, comprising:
(a) liquefying a starch-containing material into dextrins with a bacterial alpha-amylase at a temperature above the initial gelatinization temperature, wherein the starch-containing material comprises corn;
(b) saccharifying the dextrins using a glucoamylase to form a sugar;
(c) fermenting the sugar in a fermentation medium into ethanol using a yeast fermenting organism;
(d) recovering the fermentation product to form a whole stillage;
(e) separating the whole stillage into thin stillage and wet cake;
(e') optionally concentrating the thin stillage into syrup; and
(f) recovering oil from the thin stillage and/or optionally the syrup, wherein a protease having at least 60% sequence identity to the amino acid sequence of SEQ ID NO: 4 is added during step (d).

10. The process of claim 9, wherein the oil is recovered during and/or after step (a).

11. The process of claim 10, wherein oil recovery is increased higher than control.

12. The process of claim 9, wherein the oil is recovered from the thin stillage.

13. The process of claim 12, wherein oil recovery is increased higher than control.

14. The process of claim 9, wherein the oil is optionally recovered from the syrup.

15. The process of claim 14, wherein oil recovery is increased higher than control.

16. The process of claim 9, wherein the bacterial alpha-amylase is the *Bacillus stearothermophilus* alpha-amylase having the sequence of SEQ ID NO: 1 herein, which is truncated to have from 485-495 amino acids, or one having at least 70% sequence identity thereto.

17. A process of recovering oil, comprising:
(a) liquefying a starch-containing material into dextrins with a bacterial alpha-amylase at a temperature above the initial gelatinization temperature, wherein the starch-containing material comprises corn;
(b) saccharifying the dextrins using a glucoamylase to form a sugar;
(c) fermenting the sugar in a fermentation medium into ethanol using a yeast fermenting organism;
(d) recovering the fermentation product to form a whole stillage;
(e) separating the whole stillage into thin stillage and wet cake;
(e') optionally concentrating the thin stillage into syrup; and
(f) recovering oil from the thin stillage and/or optionally the syrup, wherein a protease having at least 60% sequence identity to the amino acid sequence of SEQ ID NO: 4 is added during step (e).

18. The process of claim 17, wherein the oil is recovered during and/or after step (a).

19. The process of claim 18, wherein oil recovery is increased higher than control.

20. The process of claim 17, wherein the oil is recovered from the thin stillage.

21. The process of claim 20, wherein oil recovery is increased higher than control.

22. The process of claim 17, wherein the oil is optionally recovered from the syrup.

23. The process of claim 22, wherein oil recovery is increased higher than control.

24. The process of claim 17, wherein the bacterial alpha-amylase is the *Bacillus stearothermophilus* alpha-amylase having the sequence of SEQ ID NO: 1 herein, which is truncated to have from 485-495 amino acids, or one having at least 70% sequence identity thereto.

* * * * *